US008267868B2

(12) United States Patent
Taylor et al.

(10) Patent No.: US 8,267,868 B2
(45) Date of Patent: Sep. 18, 2012

(54) SINGLE-INSERTION, MULTIPLE SAMPLE BIOPSY DEVICE WITH INTEGRATED MARKERS

(75) Inventors: Jon Taylor, Groton, MA (US); Stanley O. Thompson, New Boston, NH (US); Timothy J. Coonahan, Sterling, MA (US); Gregory A. Gray, Knoxville, TN (US)

(73) Assignee: C. R. Bard, Inc., Murray Hill, NJ (US)

( * ) Notice: Subject to any disclaimer, the term of this patent is extended or adjusted under 35 U.S.C. 154(b) by 831 days.

(21) Appl. No.: 11/997,405

(22) PCT Filed: Aug. 10, 2006

(86) PCT No.: PCT/US2006/031327
§ 371 (c)(1),
(2), (4) Date: Jul. 7, 2008

(87) PCT Pub. No.: WO2007/021905
PCT Pub. Date: Feb. 22, 2007

(65) Prior Publication Data
US 2008/0319341 A1    Dec. 25, 2008

Related U.S. Application Data

(60) Provisional application No. 60/707,229, filed on Aug. 10, 2005.

(51) Int. Cl.
*A61B 10/00* (2006.01)
(52) U.S. Cl. ........ 600/564; 600/565; 600/566; 600/567; 600/568

(58) Field of Classification Search .......... 600/564–568, 600/562; 606/167, 170–171; 604/164.01, 604/164.11–164.12
See application file for complete search history.

(56) References Cited

U.S. PATENT DOCUMENTS

| 737,293 | A | 8/1903 | Summerfeldt |
| 1,585,934 | A | 5/1926 | Muir |
| 1,663,761 | A | 3/1928 | Johnson |
| 2,953,934 | A | 9/1960 | Sundt |
| 3,019,733 | A | 2/1962 | Braid |
| 3,224,434 | A | 12/1965 | Molomut et al. |
| 3,477,423 | A | 11/1969 | Griffith |
| 3,512,519 | A | 5/1970 | Hall |
| 3,561,429 | A | 2/1971 | Jewett et al. |
| 3,565,074 | A | 2/1971 | Foti |
| 3,606,878 | A | 9/1971 | Kellogg |
| 3,727,602 | A | 4/1973 | Hyden et al. |
| 3,732,858 | A | 5/1973 | Banko |
| 3,800,783 | A | 4/1974 | Jamshidi |
| 3,844,272 | A | 10/1974 | Banko |
| 3,882,849 | A | 5/1975 | Jamshidi |
| 4,275,730 | A | 6/1981 | Hussein |
| 4,282,884 | A | 8/1981 | Boebel |
| 4,354,092 | A | 10/1982 | Manabe et al. |
| 4,445,509 | A | 5/1984 | Auth |
| 4,490,137 | A | 12/1984 | Moukheibir |

(Continued)

FOREIGN PATENT DOCUMENTS
DE    3924291 A1    1/1991
(Continued)

*Primary Examiner* — Max Hindenburg
*Assistant Examiner* — H. Q. Nguyen

(57) ABSTRACT

The present invention provides for exemplary embodiments of a single-insertion, multiple sample biopsy device. Exemplary embodiments of a single-insertion, multiple sampling device with integrated marker release.

7 Claims, 16 Drawing Sheets

U.S. PATENT DOCUMENTS

| | | |
|---|---|---|
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,617,430 A | 10/1986 | Bryant |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| 33,258 A | 7/1990 | Onik et al. |
| 4,940,061 A | 7/1990 | Terwilliger et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,125,413 A | 6/1992 | Baran |
| 5,138,245 A | 8/1992 | Mattinger et al. |
| 5,158,528 A | 10/1992 | Walker et al. |
| 5,176,628 A | 1/1993 | Charles et al. |
| 5,225,763 A | 7/1993 | Krohn et al. |
| 5,234,000 A | 8/1993 | Hakky et al. |
| 5,236,334 A | 8/1993 | Bennett |
| 5,282,477 A | 2/1994 | Bauer |
| 5,324,306 A | 6/1994 | Makower et al. |
| 5,334,183 A | 8/1994 | Wuchinich |
| 5,368,029 A | 11/1994 | Holcombe et al. |
| 5,368,045 A | 11/1994 | Clement et al. |
| 5,400,798 A | 3/1995 | Baran |
| 5,439,474 A | 8/1995 | Li |
| 5,458,112 A | 10/1995 | Weaver |
| 5,479,486 A | 12/1995 | Saji |
| 5,485,917 A | 1/1996 | Early |
| 5,492,130 A | 2/1996 | Chiou |
| 5,496,860 A | 3/1996 | Matsumoto et al. |
| 5,511,556 A | 4/1996 | DeSantis |
| 5,526,822 A | 6/1996 | Burbank |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,569,284 A | 10/1996 | Young et al. |
| 5,575,293 A | 11/1996 | Miller et al. |
| 5,601,585 A | 2/1997 | Banik et al. |
| 5,602,449 A | 2/1997 | Krause et al. |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,699,909 A | 12/1997 | Foster |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,908,233 A | 6/1999 | Heskett et al. |
| 5,913,857 A | 6/1999 | Ritchart et al. |
| 5,916,229 A | 6/1999 | Evans |
| 5,928,164 A | 7/1999 | Burbank |
| 5,944,673 A | 8/1999 | Gregoire |
| 5,951,490 A | 9/1999 | Fowler |
| 5,951,575 A | 9/1999 | Bolduc et al. |
| 5,964,716 A | 10/1999 | Gregoire |
| 5,971,939 A | 10/1999 | DeSantis et al. |
| 5,976,164 A | 11/1999 | Bencini et al. |
| 5,980,469 A | 11/1999 | Burbank et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,055,870 A | 5/2000 | Jaeger |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,436,054 B1 | 8/2002 | Viola et al. |
| 6,482,158 B2 | 11/2002 | Mault |
| 6,485,436 B1 | 11/2002 | Truckai |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 * | 7/2003 | Smith et al. .................. 604/181 |
| 6,638,235 B2 | 10/2003 | Miller et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |

| | | |
|---|---|---|
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,025,732 B2 | 4/2006 | Thompson et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,828,746 B2 | 11/2010 | Teague |
| 7,854,706 B2 | 12/2010 | Hibnner |
| 7,883,476 B2 | 2/2011 | Miller et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0029007 A1 | 3/2002 | Bryan et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0156395 A1 | 10/2002 | Stephens et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0167427 A1 | 8/2004 | Quick et al. |
| 2004/0186393 A1 | 9/2004 | Leigh et al. |
| 2004/0215103 A1 | 10/2004 | Mueller, Jr. et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0236180 A1 | 10/2007 | Rodgers |
| 2007/0239067 A1 | 10/2007 | Hlbner et al. |
| 2007/0255173 A1 | 11/2007 | Hibner |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |

| | | | |
|---|---|---|---|
| 2009/0030405 A1 | 1/2009 | Quick et al. | |
| 2009/0062624 A1 | 3/2009 | Neville | |
| 2009/0082695 A1 | 3/2009 | Whitehead | |
| 2009/0125062 A1 | 5/2009 | Arnin | |
| 2009/0137927 A1 | 5/2009 | Miller | |
| 2009/0227893 A1 | 9/2009 | Coonahan et al. | |
| 2010/0063416 A1 | 3/2010 | Cicenas et al. | |
| 2010/0106053 A1 | 4/2010 | Videbaek et al. | |
| 2010/0152611 A1 | 6/2010 | Parihar et al. | |
| 2010/0160820 A1 | 6/2010 | Weikel, Jr. et al. | |
| 2010/0210966 A1 | 8/2010 | Videbaek | |
| 2010/0292607 A1 | 11/2010 | Moore et al. | |
| 2010/0312140 A1 | 12/2010 | Smith et al. | |
| 2011/0152715 A1 | 6/2011 | Delap et al. | |
| 2011/0160611 A1 | 6/2011 | Ritchart et al. | |

FOREIGN PATENT DOCUMENTS

| | | |
|---|---|---|
| DE | 4041614 C1 | 10/1992 |
| DE | 10034297 A1 | 4/2001 |
| DE | 10026303 A1 | 2/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1665989 A2 | 6/2006 |
| EP | 2095772 A1 | 9/2009 |
| EP | 2106750 A2 | 10/2009 |
| FR | 1345429 A | 12/1963 |
| FR | 2739293 A1 | 4/1997 |
| GB | 2018601 A | 10/1979 |
| JP | 10508504 A | 8/1998 |
| JP | 2007502159 A | 2/2007 |
| WO | 9624289 A2 | 8/1996 |
| WO | 9628097 A1 | 9/1996 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008024684 A2 | 2/2008 |
| WO | 2008040812 A1 | 4/2008 |
| WO | 2008131362 A2 | 10/2008 |

* cited by examiner

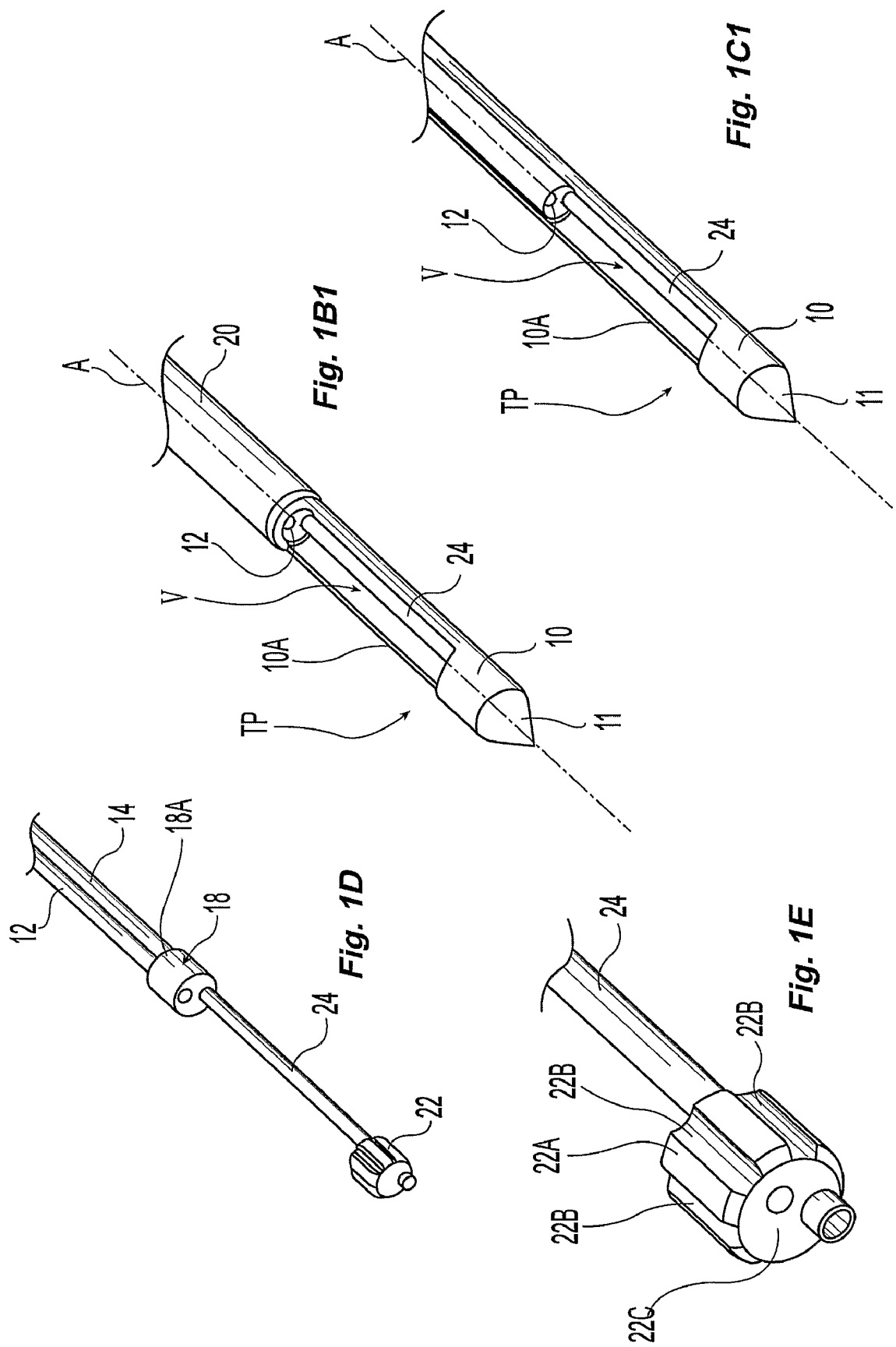

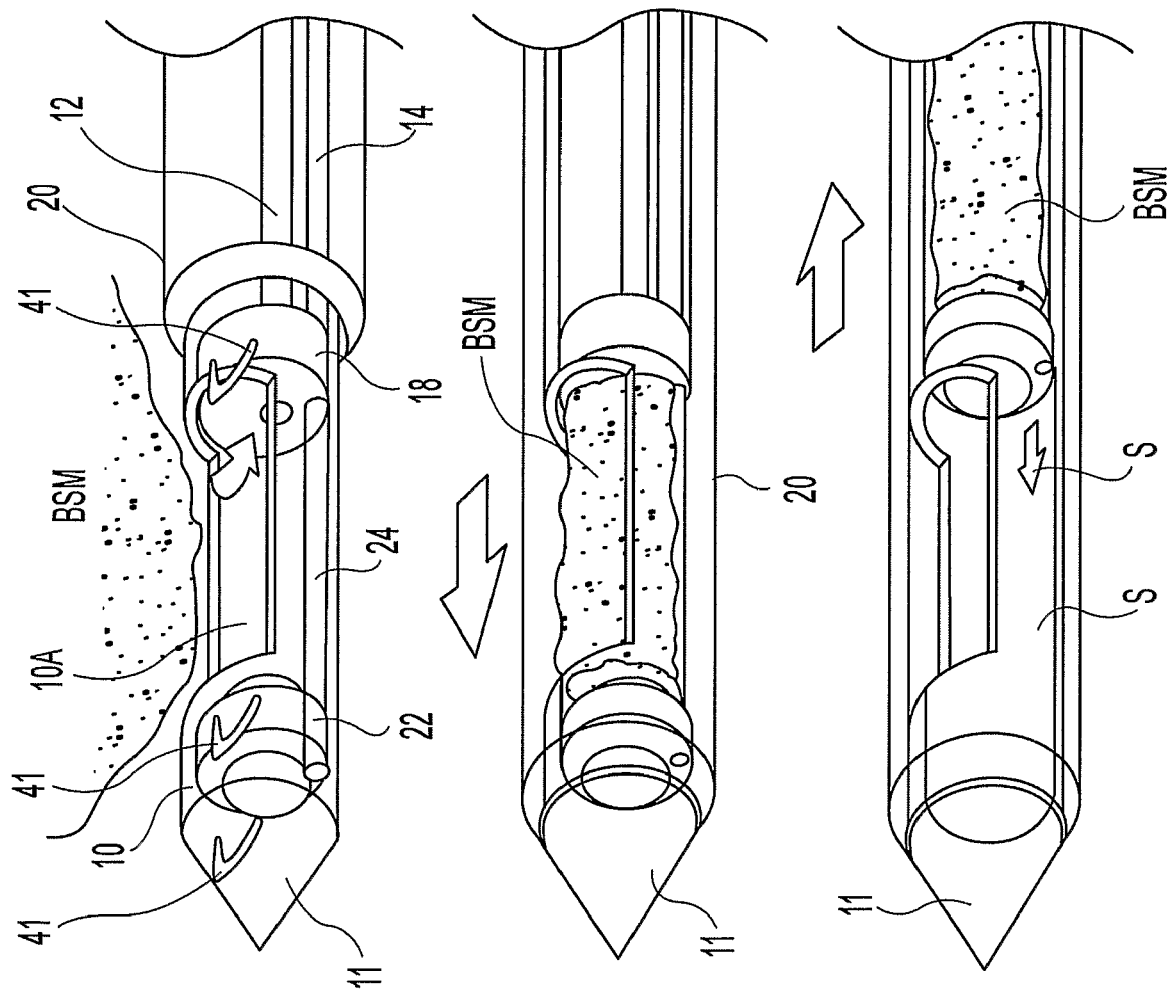

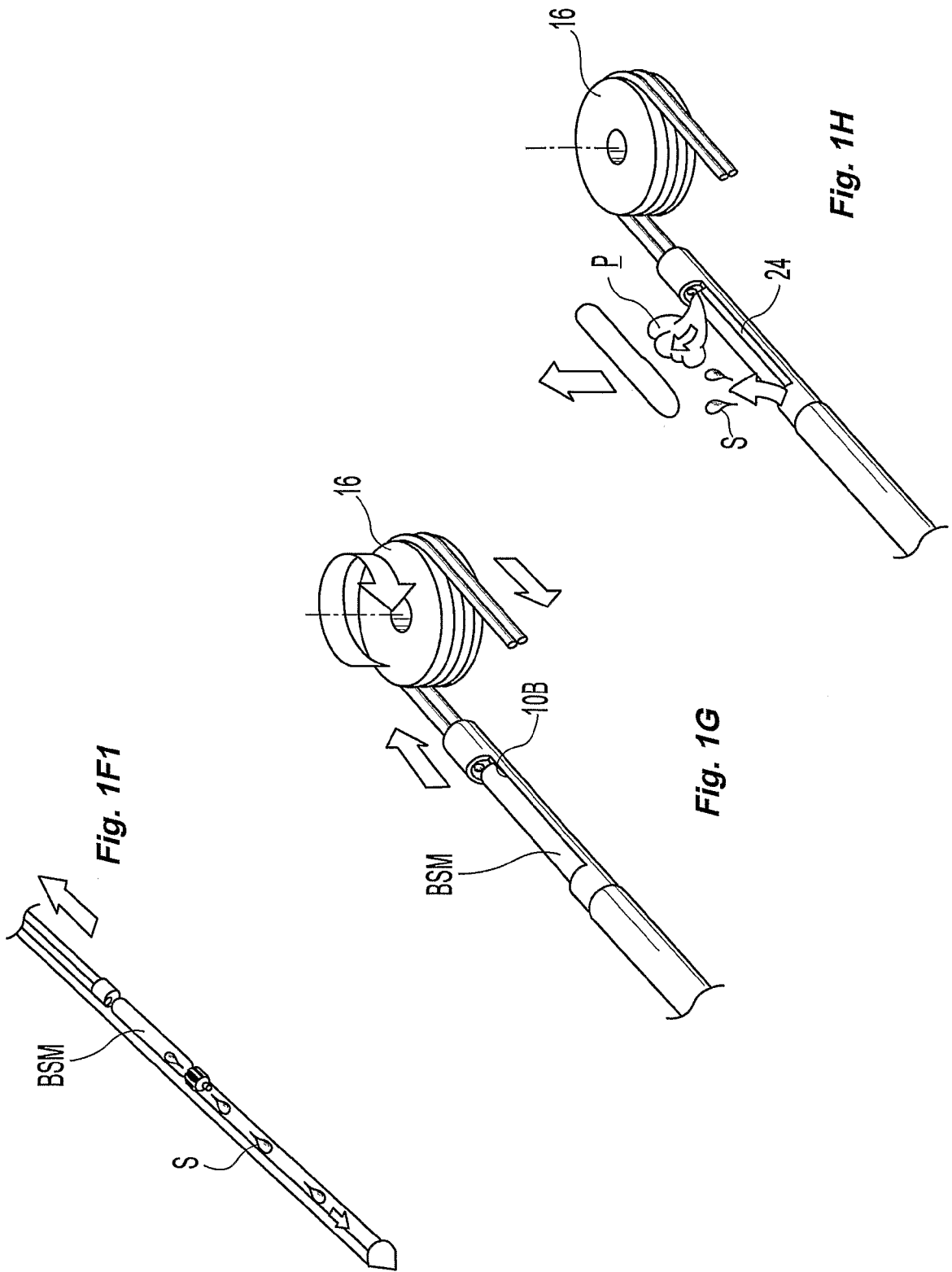

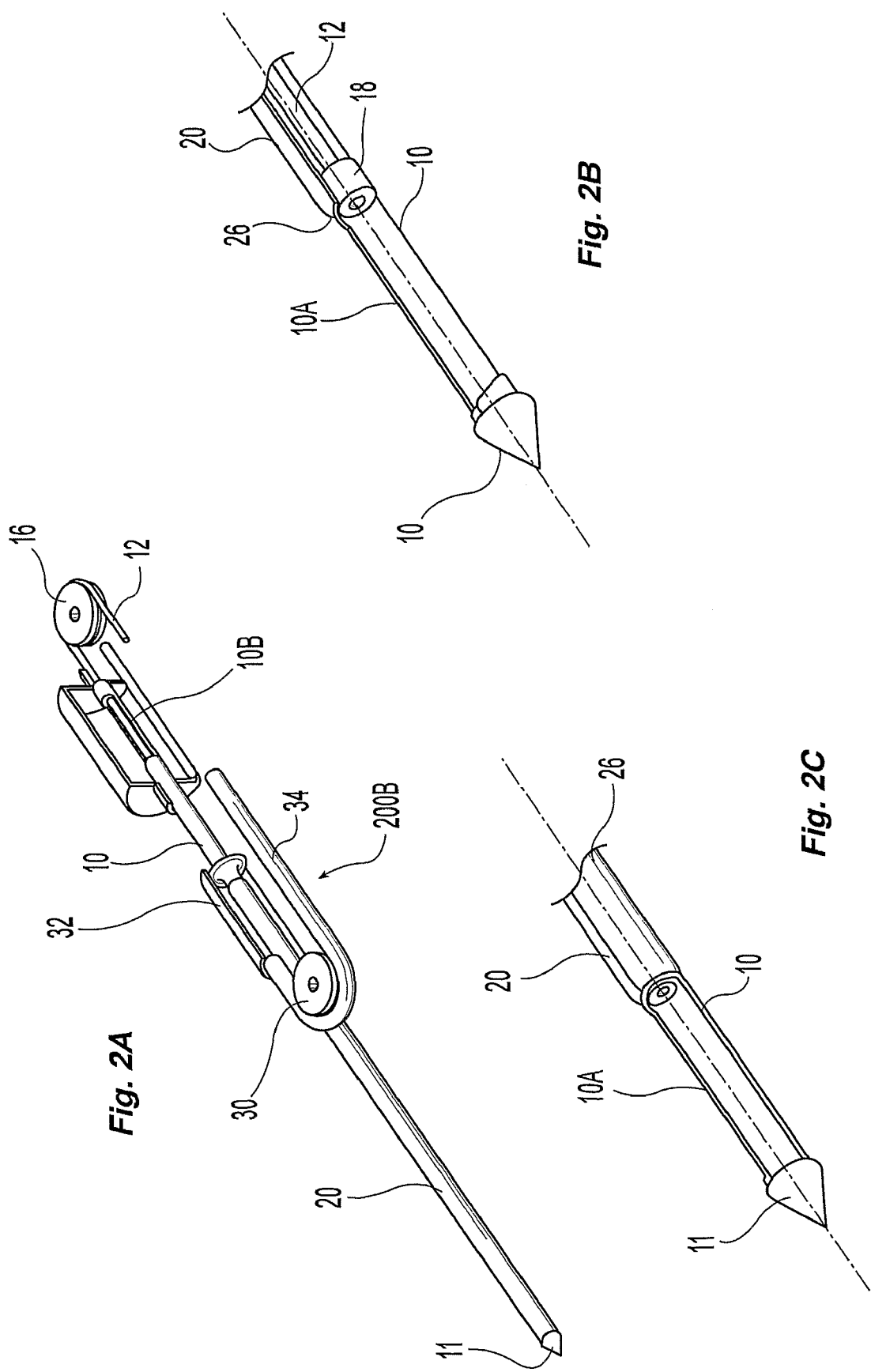

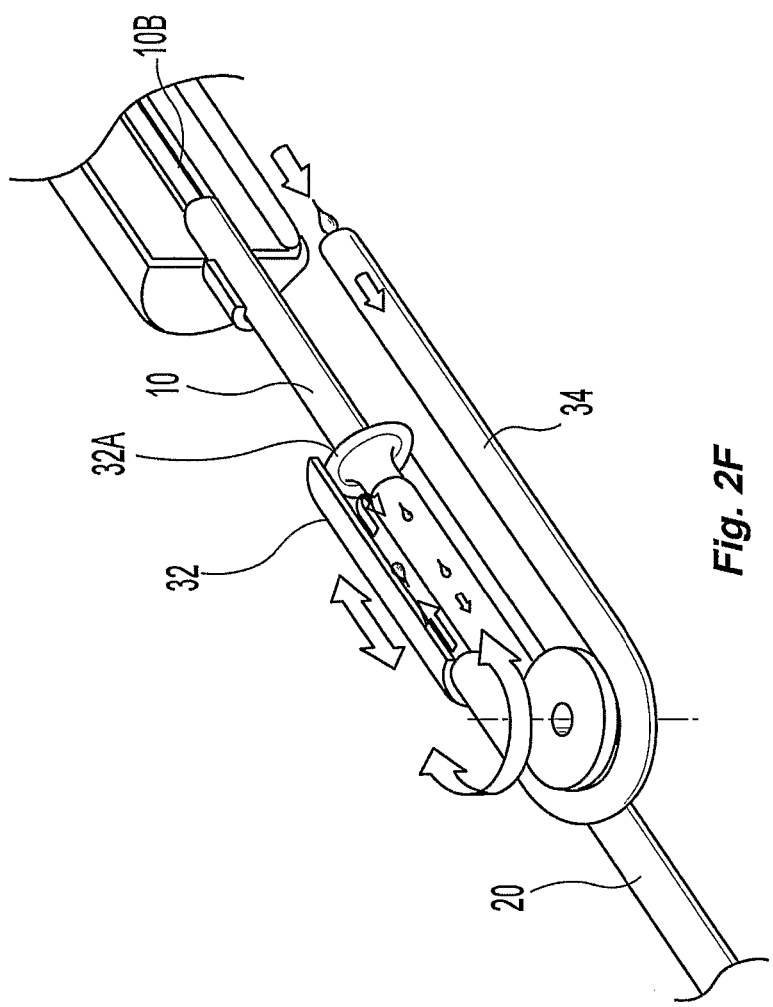
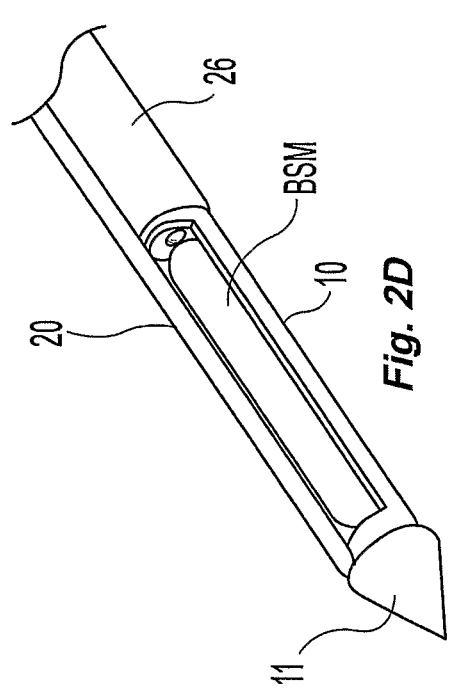
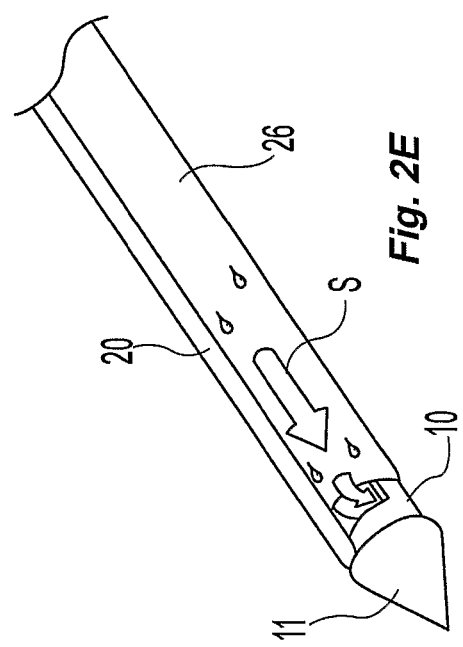

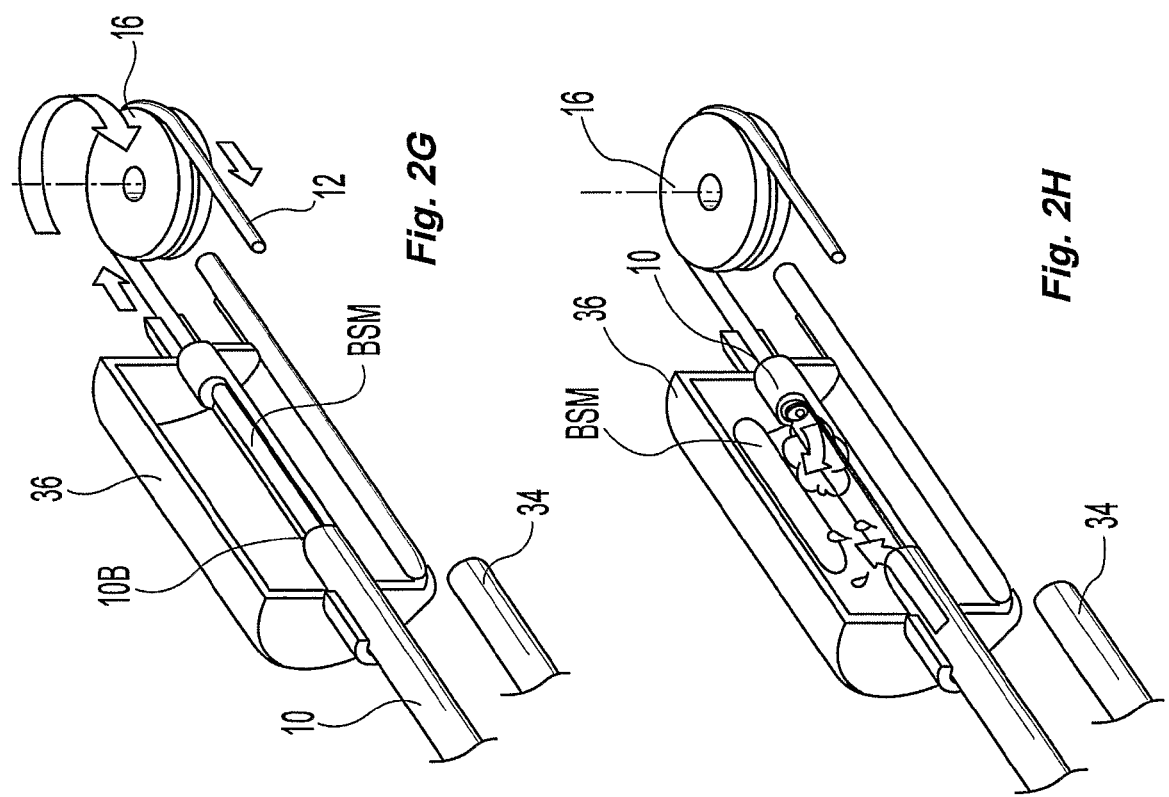

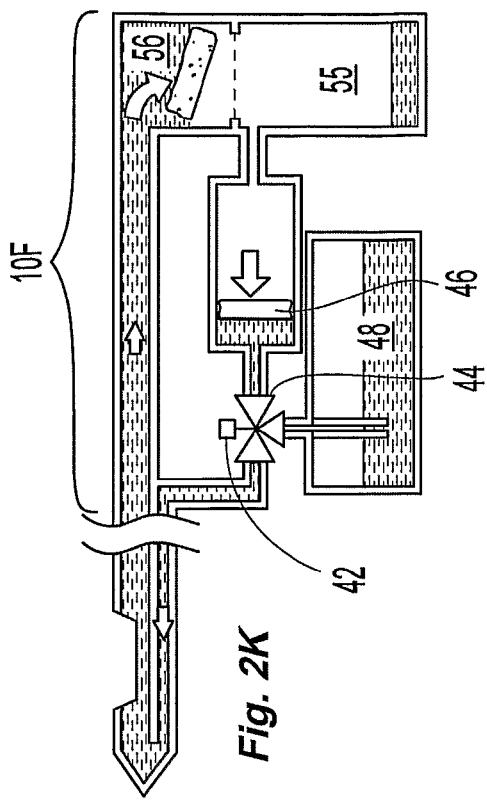
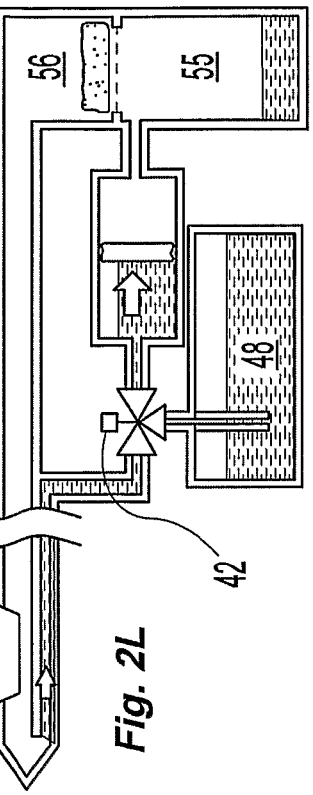
Fig. 2K
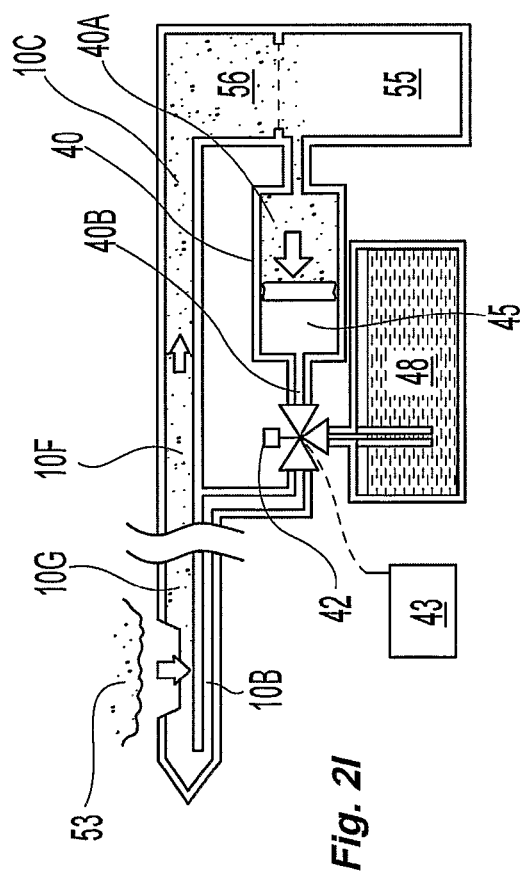
Fig. 2I
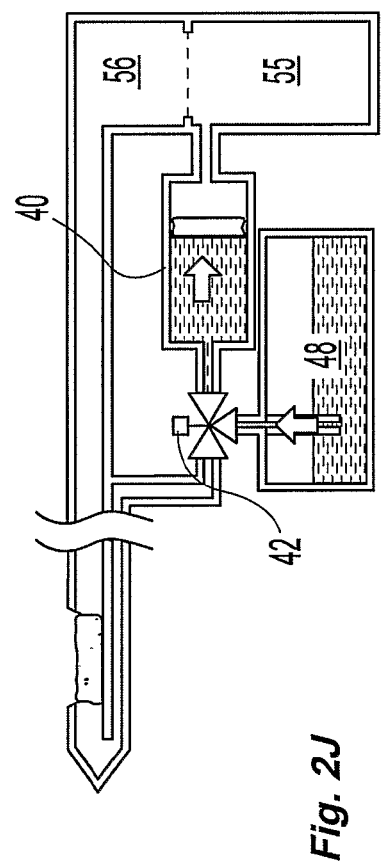
Fig. 2L
Fig. 2J

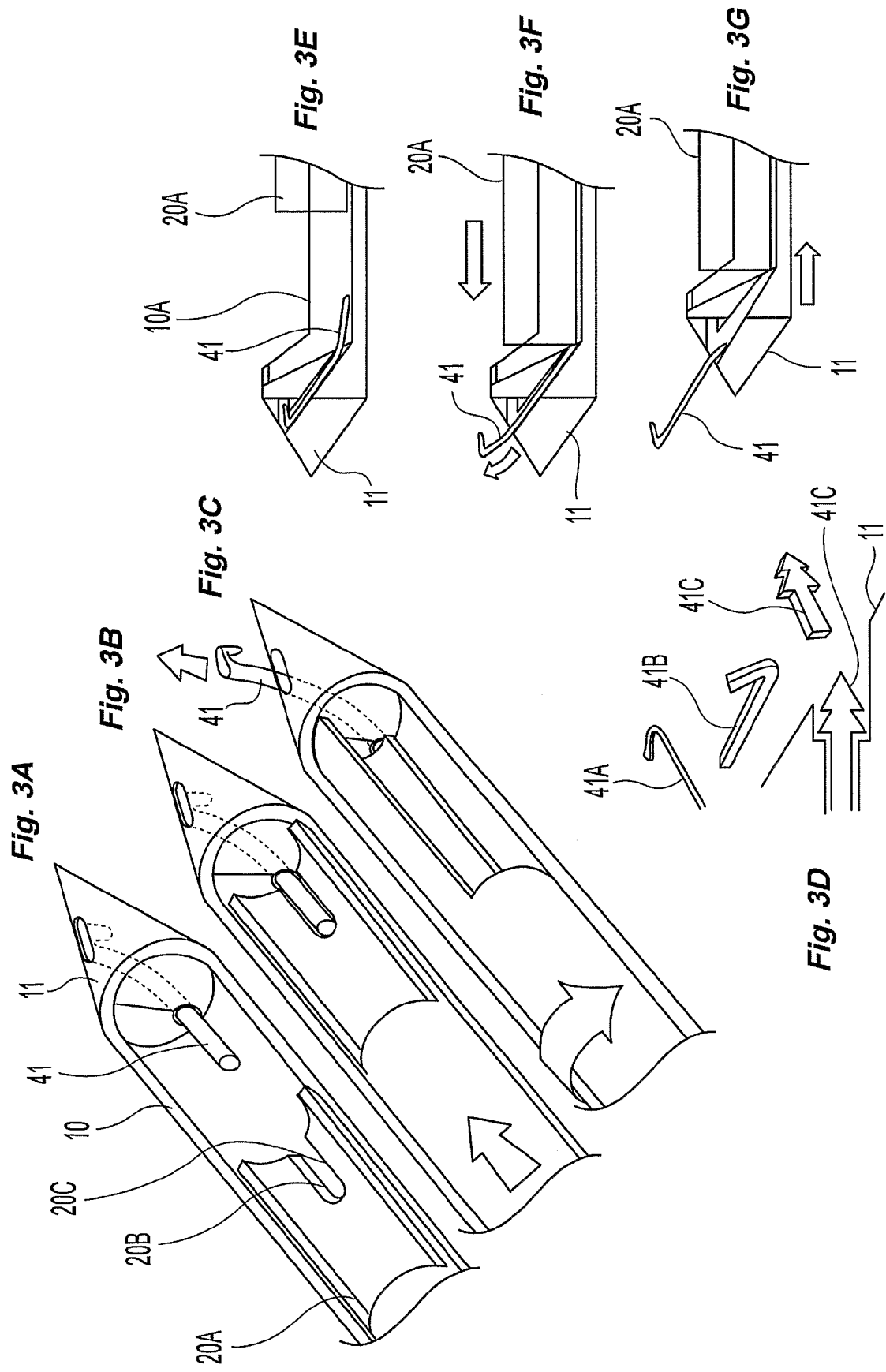

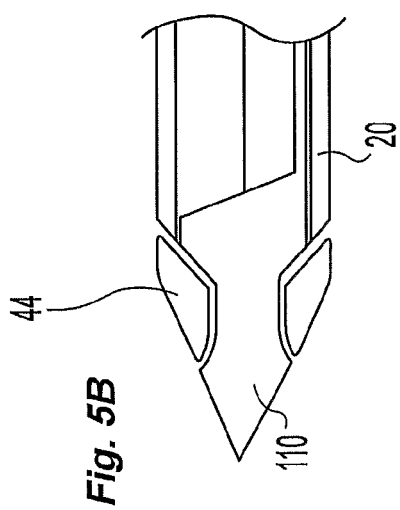
*Fig. 5B*
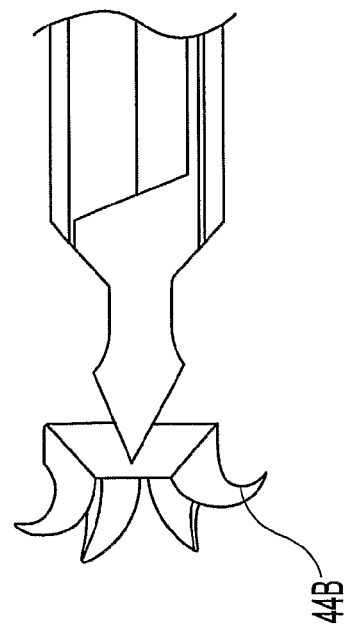
*Fig. 5C*
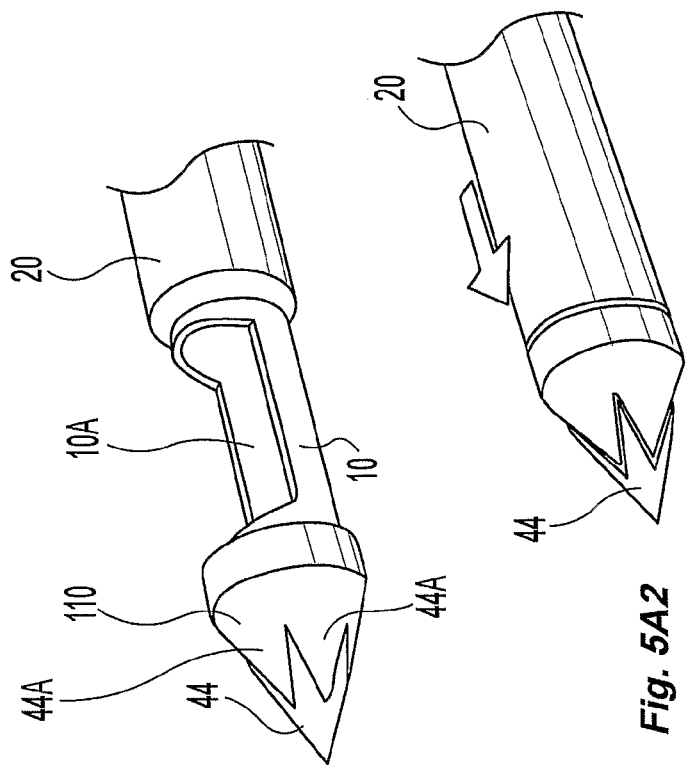
*Fig. 5A1*
*Fig. 5A2*
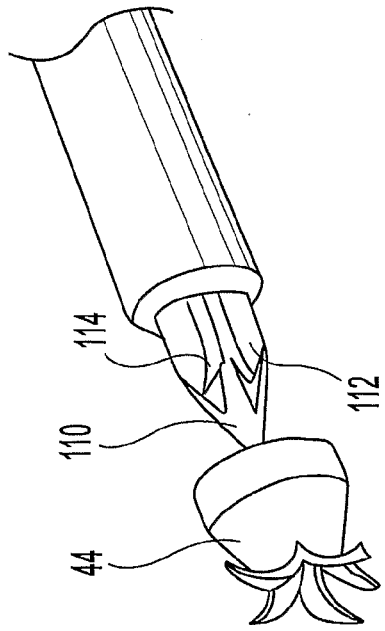
*Fig. 5A3*

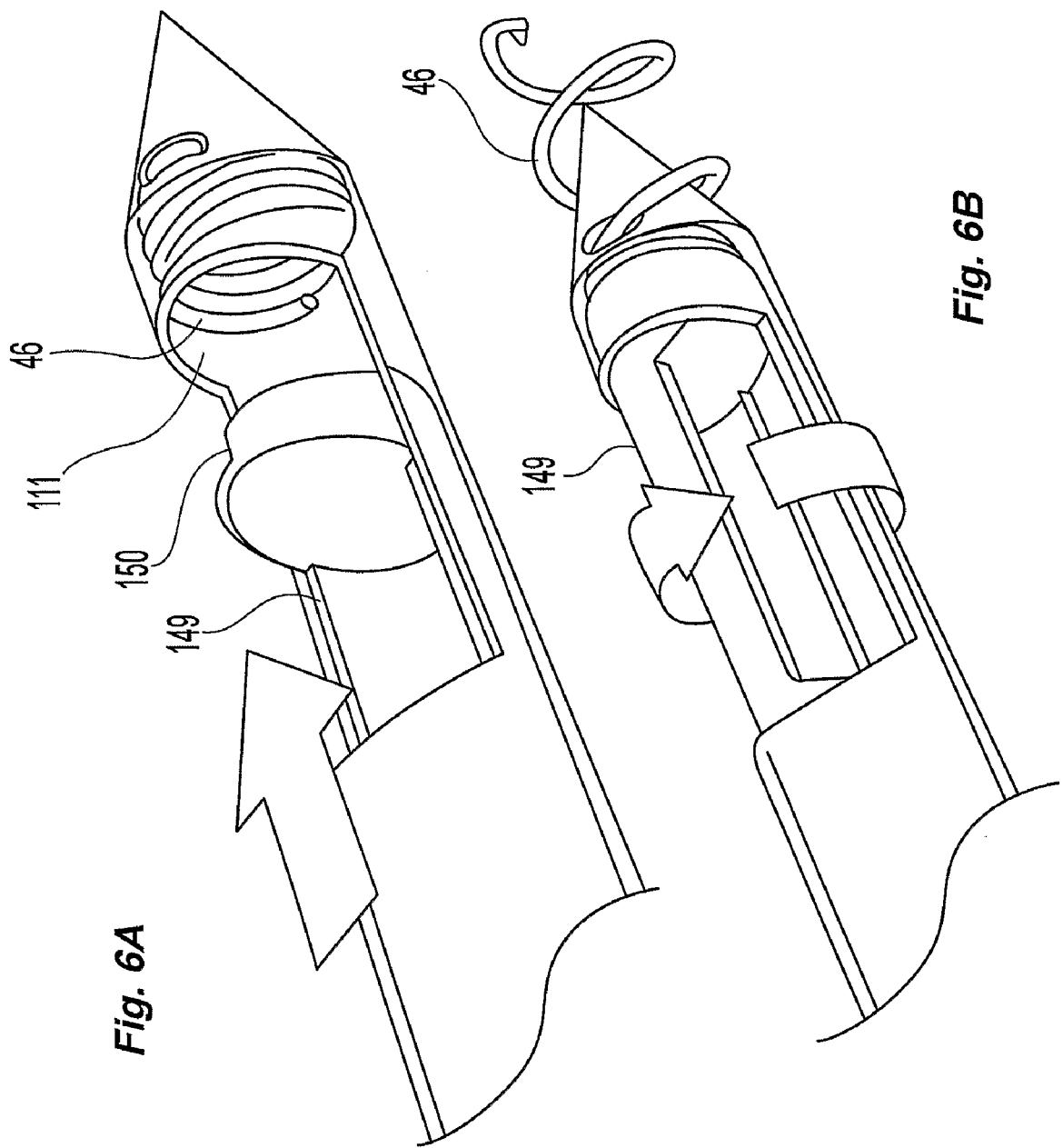

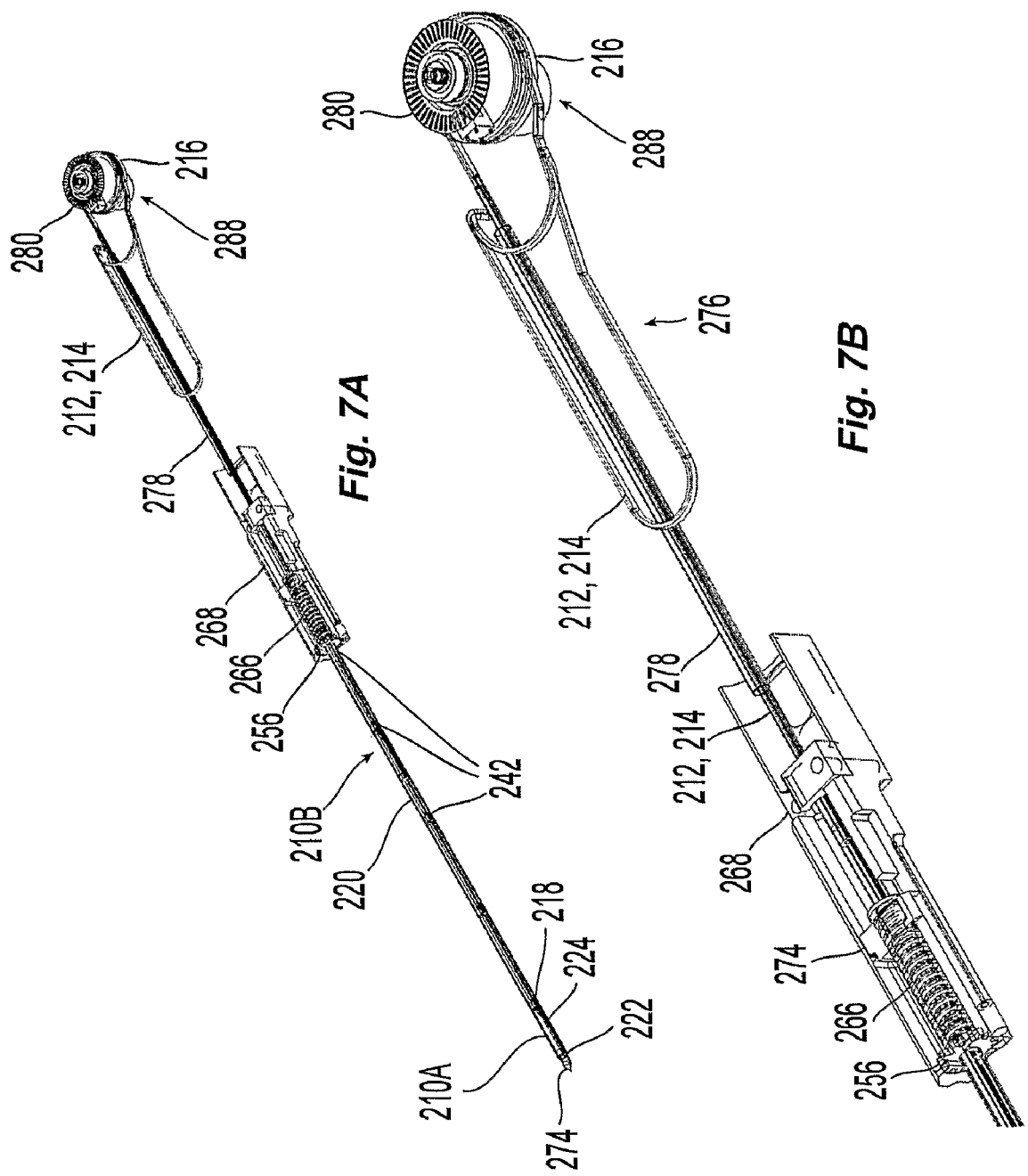

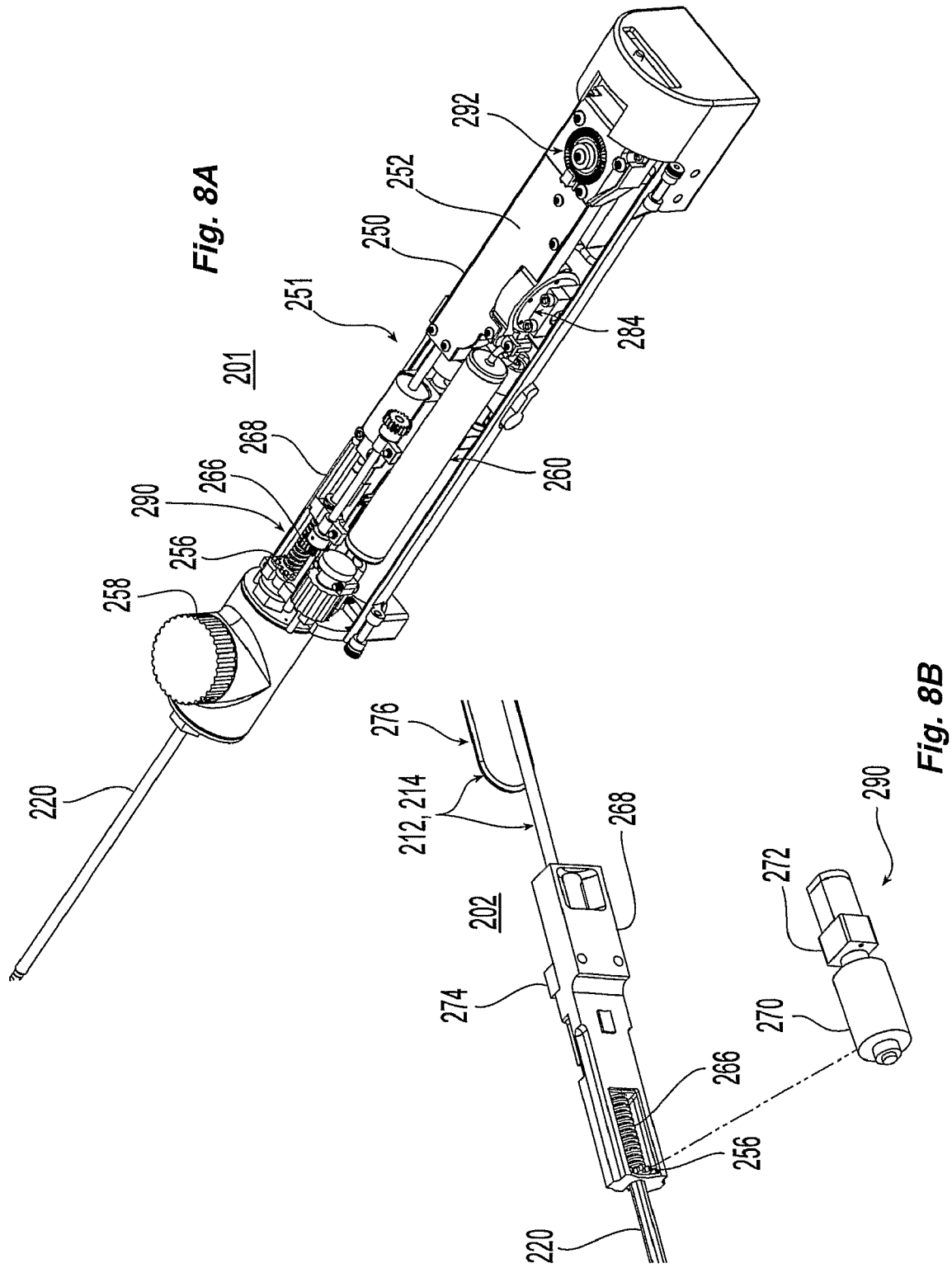

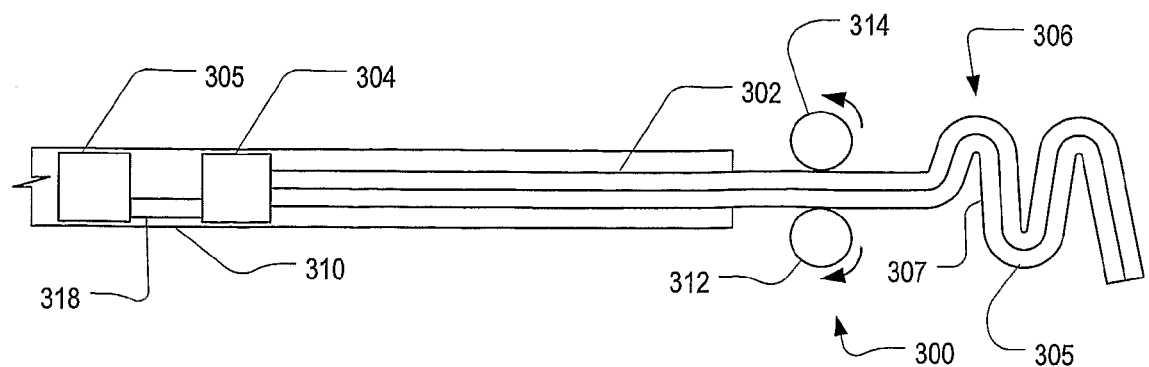
*Fig. 9*
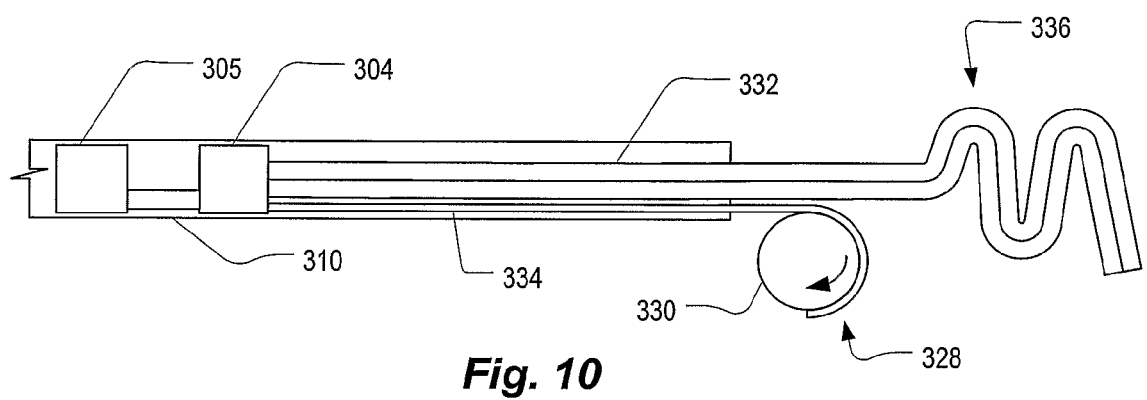
*Fig. 10*
Controller 350
*Fig. 11*

SINGLE-INSERTION, MULTIPLE SAMPLE BIOPSY DEVICE WITH INTEGRATED MARKERS

PRIORITY DATA AND INCORPORATION BY REFERENCE

This application is a 35 U.S.C. 371 application of International Application No. PCT/US2006/031327, filed Aug. 10, 2006, which claims priority to U.S. Provisional Patent Application No. 60/707,229, filed Aug. 10, 2005, the entireties of which are hereby incorporated by reference.

FIELD OF THE INVENTION

This invention relates to a tissue biopsy sampling device.

BACKGROUND OF THE INVENTION

Often, it is either desirable or necessary to obtain specimens of tissue from humans and other animals, particularly in the diagnosis and treatment of patients with cancerous tumors, premalignant conditions, and other diseases or disorders. For example, when it is discovered that suspicious conditions exist, either by means of x-ray or ultrasound imaging in various tissues of the body, a physician typically performs a biopsy to determine if the cells at the suspected site are cancerous.

A biopsy can be done either by an open or percutaneous technique. Open biopsy is an invasive procedure using a scalpel, whereby either a portion (incisional biopsy) or the entire mass (excisional biopsy) is removed. Percutaneous biopsy is usually done with a needle-like instrument through a relatively small incision, and can be performed by fine needle aspiration (FNA) or through the taking of a core biopsy sample. In FNA biopsy, individual cells or clusters of cells are obtained for cytologic examination and can be prepared such as in a Papanicolaou smear. In a core biopsy, a core or fragment of the tissue is obtained for histologic examination.

Intact tissue from the organ, lesion, or tumor is preferred by medical personnel in order to arrive at a definitive diagnosis regarding the patient's condition. In most cases only part of the tissue in question needs to be sampled. The portions of tissue extracted must be indicative of the organ, lesion, or tumor as a whole. Often, multiple tissue samples from various locations of the mass being sampled may be taken.

The percutaneous biopsy procedure can be performed utilizing various techniques and devices. One such biopsy device can include an inner stylet positioned inside an cutting cannula, whereby the stylet is able to slide into and out of the cannula. The stylet can be a solid, pointed needle having a tissue sampling recess, and the cannula can be a hollow, open-ended needle having a sharp tip. The stylet and cannula can be manipulated cooperatively to capture a tissue sample in the sample recess. Such existing devices can be manually operated, semi-automated, and automated.

U.S. Pat. No. 6,485,436 shows a multiple sample biopsy needle with a hydraulic mechanism that circulates fluid from the tip of the needle back to a receiving basket or baskets. A revolver-type array of receiving chambers is disclosed.

U.S. Pat. No. 5,827,305 shows a tissue sampling needle that pushes a sample proximally using a saline wash. Samples remain spaced apart within the needle such that the sequence of their collection is preserved. Samples can also be removed from a port while the needle remains in place. No mechanical transport mechanisms or drives are disclosed.

U.S. Pat. No. 5,526,822 shows a transport system that uses a cannula and knock-out pin combined with a vacuum source to shuttle a tissue sample to a multiple-chamber cassette where it is knocked out. The cannula is then repositioned for another sample. The vacuum source is external. A revolving sample cassette is also shown. A vent opening in each sample cylinder of the cassette is provided to eject the fluid used to transport the tissue sample. A removable disposable needle-bearing cassette interfaces with rotary and linear drives by means of long gears and shuttles that cradle the gears. Cutters operate in rotary and linear fashion (a counter-rotating cutters embodiment is included) and the cannula can be rotated to orient the sample opening.

U.S. Pat. No. 6,017,316 shows a transport system similar to U.S. Pat. No. 5,827,822 in which a cutter transports with vacuum assist. Multiple sampling with single insertion is described but not automated multiple sample-handling. The details of a drive system are not disclosed U.S. Pat. No. 6,193,673 shows a needle with a durable part and a disposable part. An external cutting cannula rotates and advances axially to cut a sample. The tissue cutter is driven axially by a rack and pinion drive which are part of a durable component. A cradle connects the rack to the cutting cannula.

U.S. Pat. No. 5,944,673 describes a tissue extractor that rotates within a piercing needle to align with any one of multiple receiving ports while obstructing the remaining ports. The tissue sample is cut by advancing the cutter and removing by withdrawing the extractor. A vacuum holds the tissue sample in place during the removal of the tissue extractor from the cutter. The cutter rotates as it advances.

It is known to obtain a single sample with a single insertion. However, there are circumstances where there may be a need to obtain more than one samples. While the known biopsy needle can be re-inserted multiple times, such technique can cause pain and scarring of the body site.

It is known to leave a marker at the biopsied site. To do so, however, a physician or healthcare provider would typically need to withdraw the biopsy needle and insert a different device to leave a marker at the biopsied site. The additional step and device may not allow the marker to be deposited at the actual biopsied site, which can lead to inaccurate post-biopsy diagnosis.

SUMMARY OF THE INVENTION

The present invention provides for exemplary embodiments of a single-insertion, multiple sample biopsy device. The present invention also provides for exemplary embodiments of a single-insertion, multiple sampling device with integrated marker release.

In one aspect, a single-insertion, multiple sample biopsy device is provided that includes a stylet, a cannula, a plurality of lumens including flexible and rigid portions, first and second bulkheads, and a transport subassembly. The stylet extends along a longitudinal axis between a distal end and a proximal end, the stylet having a tip at the distal end and a hollow interior volume extending from a biopsy port proximate the distal end to the proximal end. The cannula surrounds a portion of the stylet and is movable along the longitudinal axis. The plurality of lumens is disposed in the interior volume. The rigid lumen is coupled to one of the plurality of lumens. The first bulkhead is disposed near the proximal end. The first bulkhead is coupled to the lumens and a second bulkhead disposed near the distal end. The second bulkhead is coupled to the rigid lumen, and both bulkheads define a biopsy sample volume. The transport subassembly is coupled to the first and second bulkheads to move a biopsy sample from the biopsy port to the proximal end of the stylet.

In yet another aspect, a single-insertion, multiple sample biopsy device is provided that includes a stylet, cannula, sleeve, lumen, bulkhead and transport subassembly. The stylet extends along a longitudinal axis between a distal end and a proximal end. The stylet has a tip at the distal end and a hollow interior volume that extends from a biopsy port proximate the distal end to the proximal end. The cannula surrounds a portion of the stylet and is movable along the longitudinal axis. The sleeve is disposed between the stylet and the cannula. The lumen is disposed in the interior volume of the stylet. The bulkhead is coupled to a distal end of the lumen. The transport subassembly is coupled to the lumen and the sleeve to move the bulkhead and sleeve relative to each other along the longitudinal axis between the proximal and distal ends. Preferably, at least a portion of the lumen is flexible.

In yet a further aspect, a method of sampling biological tissue with a biopsy device is provided. The device has a tissue trough coupled to at least one lumen disposed in a needle that extends along a longitudinal axis between a distal end and a proximal end. The method can be achieved by: capturing a biological sample in longitudinal aperture defined on a circumference of the needle; and translating said at least one lumen through the interior of the needle to transport the biological sample from the distal to the proximal ends.

According to an embodiment, the invention is a single-insertion, multiple sample biopsy device with a stylet extending along a longitudinal axis between a distal end and a proximal end. The stylet can have a tip at the distal end and a hollow interior volume extending from a biopsy port proximate the distal end to the proximal end. A cannula surrounds a portion of the stylet and is movable along the longitudinal axis. There are lumens in the interior volume. A first bulkhead is disposed near the proximal end and coupled to the lumens. A second bulkhead is disposed near the distal end and coupled to one of the lumens. Both bulkheads defines a biopsy sample volume. A transport subassembly is coupled to the first and second bulkheads to move a biopsy sample from the biopsy port to the proximal end of the stylet.

The transport subassembly preferably includes one or both of a vacuum and pressurized fluid supply in fluid communication with one of the lumens and a pulley coupled to the bulkheads and lumens to move the bulkheads and lumens along the longitudinal axis as a single unit. The first bulkhead is preferably configured to confront the interior surface of the stylet and the second bulkhead preferably is configured to permit fluid flow between the outer perimeter of the bulkhead and the interior surface of the stylet.

According to another embodiment, the invention is a single-insertion, multiple sample biopsy device that includes a stylet extending along a longitudinal axis between a distal end and a proximal end. The stylet has a tip at the distal end. A hollow interior volume extends from a biopsy port proximate the distal end to the proximal end. A cannula surrounds a portion of the stylet and is movable along the longitudinal axis. A sleeve is disposed between the stylet and the cannula. A lumen is disposed in the interior volume of the stylet. A bulkhead is coupled to a distal end of the lumen. A transport subassembly is coupled to the lumen and the sleeve to move the bulkhead and sleeve relative to each other along the longitudinal axis between the proximal and distal ends.

Preferably, the transport subassembly includes a first pulley coupled to the sleeve via a member and a second pulley coupled to the bulkhead via the lumen. Also, preferably, the member is in fluid communication with a pressurized saline source and the lumen is in fluid communication with one or more of a vacuum and pressurized fluid source. The stylet tip can have a marker one of the tip and a bulkhead disposed in the stylet. The marker is ejected from at least one of the tip and the bulkhead in an operative condition of the device.

Preferably, the stylet tip includes a marker mounted on the outer surface of the tip. The marker is separated from the tip in an operative condition of the device. The marker is one or more of a hooked marker, helical marker and serrated edge marker. The marker can also be an annular marker or a split-ring marker.

According to another embodiment, the invention is a method of sampling biological tissue with a biopsy device that has a tissue trough coupled to at least one lumen disposed in a needle that extends along a longitudinal axis between a distal end and a proximal end. The method can be achieved by: capturing a biological sample in longitudinal aperture defined on a circumference of the needle; translating the at least one lumen through the interior of the needle to transport the biological sample from the distal to the proximal ends. The translating includes filling the trough defined by the interior surface of the needle is disposed about a sliding bulkhead with a bio compatible fluid.

According to another embodiment, the invention is a biopsy device with a stylet that extends along a longitudinal axis between a distal end and a proximal end. The stylet has a sample opening and an interior volume adjacent its distal end, the opening providing access to the interior volume. A longitudinal cutting member with a cutting edge is movable with respect to the stylet such that the cutting edge can cross over the sample opening to cut a tissue sample from a host. At least one lumen inside the stylet and movable along the longitudinal axis has a distal bulkhead at a distal end of the interior volume. A transport subassembly coupled to the at least one bulkhead moves a tissue sample from the sample port to the proximal end of the stylet. There is a proximal bulkhead at a proximal end of the interior volume. The transport subassembly includes a motor-drivable pulley with the at least one lumen wrapping at least partly around the motor-drivable pulley. A saline pump is connected to the at least one lumen which has an outlet in communication with the interior volume.

According to an embodiment, the invention is a single-insertion, multiple sample biopsy device with a stylet extending along a longitudinal axis between a distal end and a proximal end. The stylet has a tip at the distal end and a hollow interior volume extending from a biopsy port proximate the distal end to the proximal end. A cannula surrounds a portion of the stylet and is movable along the longitudinal axis. A plurality of lumens are located in the interior volume. A first bulkhead is located near the proximal end. The first bulkhead is coupled to the lumens. A second bulkhead is located near the distal end. The second bulkhead is coupled to the one of the lumens. Both bulkheads define a biopsy sample volume. A transport subassembly is coupled to the first and second bulkheads to move a biopsy sample from the biopsy port to the proximal end of the stylet.

Preferably, the transport subassembly includes one or both of vacuum and pressurized fluid supply in fluid communication with one of the lumens and a pulley coupled to the bulkheads and lumens to move the bulkheads and lumens along the longitudinal axis as a single unit. Also, preferably, the first bulkhead is configured to confront the interior surface of the stylet and the second bulkhead is configured to permit fluid flow between the outer perimeter of the bulkhead and the interior surface of the stylet.

According to another embodiment, the invention is single-insertion, multiple sample biopsy device that includes a stylet extending along a longitudinal axis between a distal end and a proximal end. The stylet has a tip at the distal end and a hollow interior volume extending from a biopsy port proximate the distal end to the proximal end. A cannula surrounds a portion of the stylet and movable along the longitudinal axis. A sleeve is located between the stylet and the cannula and a lumen is located in the interior volume of the stylet. A bulkhead is coupled to a distal end of the lumen. A transport subassembly is coupled to the lumen and the sleeve to move the bulkhead and sleeve relative to each other along the longitudinal axis between the proximal and distal ends.

Preferably, the transport subassembly includes a first pulley coupled to the sleeve via a member and a second pulley coupled to the bulkhead via the lumen. The member can be in fluid communication with a pressurized saline source and the lumen is in fluid communication with one or more of a vacuum and pressurized fluid source. Preferably, also, the stylet tip includes a marker located in one of the tip and a bulkhead located in the stylet. The marker is ejected from at least one of the tip and the bulkhead in an operative condition of the device.

In a variation, the stylet tip includes a marker mounted on the outer surface of the tip, the marker is separated from the tip in an operative condition of the device. The marker can be one or more of a hooked marker, helical marker and serrated edge marker. The marker can be an annular marker or a split-ring marker.

According to another embodiment, the invention is a method of sampling biological tissue with a biopsy device that has a tissue trough coupled to at least one lumen located in a needle that extends along a longitudinal axis between a distal end and a proximal end. The method can be achieved by capturing a biological sample in longitudinal aperture defined on a circumference of the needle and translating the at least one lumen through the interior of the needle to transport the biological sample from the distal to the proximal ends. Preferably the method is such that translating is done by filling the trough defined by the interior surface of the needle located about a sliding bulkhead with a bio compatible fluid.

According to an embodiment, the invention is a biopsy device with a stylet extending along a longitudinal axis between a distal end and a proximal end. The stylet has a sample opening and an interior volume adjacent its distal end, the opening providing access to the interior volume. A longitudinal cutting member has a cutting edge and is movable with respect to the stylet such that the cutting edge can cross over the sample opening to cut a tissue sample from a host. There is at least one lumen inside the stylet and movable along the longitudinal axis. The lumen has a distal bulkhead at a distal end of the interior volume. A transport subassembly is coupled to the at least one bulkhead to move a tissue sample from the sample port to the proximal end of the stylet. Preferably, a proximal bulkhead is located at a proximal end of the interior volume. The transport subassembly includes a motor-drivable pulley, the at least one lumen wrapping at least partly around the motor-drivable pulley. A saline pump is preferably connected to the at least one lumen, the lumen having an outlet in communication with the interior volume.

According to an embodiment, the invention is a single-insertion, multiple sample biopsy device, with a cannula forming at least part of an insertable biopsy needle. The cannula has a distal end where samples are received and a proximal end where samples are recovered. A shuttle mechanism, includes a distal bulkhead within the cannula. The distal bulkhead is connected to a fluid line. A mechanism feeds and retracts incremental portions of the fluid line. The fluid line is sufficiently stiff, as well as supported by the cannula, to allow the distal bulkhead to be pushed through the cannula, thereby to advance and withdraw the distal bulkhead within the cannula, whereby samples placed on a proximal side of the distal bulkhead are urged in a proximal direction by the distal bulkhead.

Preferably, the fluid line is connected to a vacuum pump at its proximal end. Preferably, the fluid line is connected to a saline pump at its proximal end. A proximal bulkhead is preferably located proximally of the distal bulkhead and connected attached to the fluid line. A vacuum line opens to a distal side of the proximal bulkhead. The fluid line opens to a distal side of the distal bulkhead. The distal bulkhead has at least one opening permitting flow from its distal side to flow backward toward its proximal side.

Preferably, there is a sample receiving chamber located at the proximal end. The receiving chamber is preferably adapted to receive and separate multiple samples, by employing such as a carousel configuration where samples drop into recesses and the chamber is rotated. An intermediate sheath is preferably provided in the cannula. The fluid line is connected to the distal bulkhead by a manifold that fluidly couples the fluid line to an annular space between the cannula and intermediate sheath.

According to an embodiment, the invention is a method of sampling biological tissue with a biopsy device that has a cutting sheath surrounding an intermediate sheath which surrounds a cannula. The cannula has a distal end with a port where tissue samples are received and a proximal end where samples are delivered. The cannula carries a movable bulkhead within it. The bulkhead is connected to a suction tube. An annular space is defined between the intermediate sheath and the cannula. The method of employing this apparatus includes: drawing a vacuum in the suction tube to suck a sample into the cannula distal end while the bulkhead is in a distal position in the cannula and moving the bulkhead proximally while fluid is forced through the annular space toward the cannula distal end and back through the cannula to transport the resected sample to the proximal end. Preferably the method includes covering the sample with the intermediate sheath. Preferably the method includes moving the intermediate sheath progressively with the sample. Preferably the method includes moving the bulkhead progressively with the intermediate sheath and the sample. Also, preferably, the method includes holding the intermediate sheath in a retracted position proximal of the port while drawing the vacuum and extending the cutting sheath by extending the cutting sheath over the port. The intermediate sheath is then extended over the port to cover the severed sample partly and the bulkhead retracted while pumping fluid distally through the annular space and proximally through the cannula to transport the sample.

According to an embodiment, the invention is a single-insertion, multiple sample biopsy device with a cutting sheath, an intermediate sheath, and a cannula all is coaxially aligned with the cutting sheath surrounding the intermediate sheath and the intermediate sheath surrounding the cannula. An annular space is defined between the intermediate sheath and the cannula. The cannula has a distal end with a port where tissue samples are received and a proximal end where samples are delivered. The intermediate sheath is movable relative to the cannula to selectively open and close the port. The cannula carries a movable bulkhead within it, the bulkhead being connected to a suction tube. A drive mechanism forces the tube along the cannula to move the bulkhead distally and proximally. A fluid pumping mechanism pumps fluid into the annular space when the intermediate sheath partly covers the port, thereby causing fluid to enter the port at a distal end thereof and flow along the cannula in a proximal direction.

Preferably, the drive mechanism and fluid pumping mechanism are operable in concert to move the intermediate sheath to partly cover the port, to move the bulkhead proximally, and to convey fluid along the annular space to the port thereby forcing a sample toward the proximal direction. Also, preferably, the biopsy device includes a vacuum pump connected to the suction tube.

According to another embodiment, the invention is a biopsy device with a stylet that has a sample extraction portion and a sample recovery position. A first bulkhead engages with, and is movable along, the stylet. A drive member attaches to the first bulkhead to move the first bulkhead between the sample extraction portion and the sample recovery position. A fluid conveyance conveys fluid into the stylet as the first bulkhead is moved from a position distal of the sample extraction portion to the sample recovery position sufficient to lubricate a tissue sample engaged by the first bulkhead as it the sample is moved along the stylet.

Preferably, the fluid conveyance generates a flow of fluid at a rate, the rate being lower than a rate required to force a tissue sample along the stylet by hydraulic pressure. Also, preferably, the drive member includes a lumen running along the stylet, the lumen forming a portion of the fluid conveyance. Also preferably, the fluid conveyance includes a lumen within the drive member. Also preferably, the device includes a frictional drive member that engages the drive member and moves it along the stylet. In another embodiment, the second bulkhead attaches to the drive member and is located proximal of the first bulkhead, the first and second bulkheads defining a sample recess between them.

According to yet another embodiment, a biopsy device has a stylet having a sample extraction portion and a sample recovery position. A drive member is movable between the sample extraction portion and the sample recovery position. A fluid conveyance conveys fluid into the stylet as the drive member is moved from a position distal of the sample extraction portion to the sample recovery position sufficient to lubricate a tissue sample engaged by the first bulkhead as it the sample is moved along the stylet. Preferably, the fluid conveyance generates a flow of fluid at a rate, the rate being lower than a rate required to force a tissue sample along the stylet by hydraulic pressure. Also, the drive member preferably includes a lumen running along the stylet, the lumen forming a portion of the fluid conveyance. Preferably, the fluid conveyance includes a lumen within the drive member. More preferably, a frictional drive member engages the drive member and moves it along the stylet.

According to yet another embodiment, a biopsy device has a stylet having a sample extraction portion and a sample recovery position. A drive member is movable between the sample extraction portion and the sample recovery position. A fluid conveyance conveys fluid into the stylet as the drive member is moved from a position distal of the sample extraction portion to the sample recovery position sufficient to fill an expanding space remaining distal of the drive member as the drive member moves from the sample extraction portion to the sample recovery position. Preferably, the fluid conveyance generates a flow of fluid at a rate, the rate being lower than a rate required to force a tissue sample along the stylet by hydraulic pressure. Also, the drive member preferably includes a lumen running along the stylet, the lumen forming a portion of the fluid conveyance. Preferably, the fluid conveyance includes a lumen within the drive member. More preferably, a frictional drive member engages the drive member and moves it along the stylet.

In the above-described embodiments, a vacuum source and a power source can be provided in a self-contained hand-held biopsy device. In all of the methods, a biopsy unit can contain a controller programmed to execute the methods automatically or contingent on consecutive command being entered through the biopsy device.

In the above-described embodiments, the one or more lumens extending through the needle (e.g., the stylet) can be, and preferably are, rigid along their length within the needle and flexible only along portions that are required to bend. This ensures that the lumens can be used to push the corresponding transport members (e.g., bulkhead(s)) for multiple sampling. In this case, flexible is intended to encompass piece-wise flexible (i.e., a combination of rigid portions linked by flexible or hinged joints) such as fluid conveyances that are made up with multiple hinged elements as links in a chain. There are known and commercially available devices that flex but provide fluid-tight flow channels.

In addition, the rigidity of the lumens can be derived from a secondary element that houses the lumen to give it rigidity, meaning a rigid portion of a lumen does not need to be a monolithic structure and the uses of terms such as "rigid lumen" or "rigid portion of a lumen" are not intended to limit the identified lumen structures to single-element structures. For example, a flexible lumen can be guided by a rigid member (for example it can slide within a tube) giving it all the effective rigidity needed to enable the lumen to move a transport member distally within a needle. Or a flexible tube can have a moving rigid guide (tube or other structure) to which it is fixedly attached, to give it all the effective rigidity needed to enable the lumen to move a transport member distally within a needle.

In addition, also in the above-described embodiments, instead of winding the proximal end or ends of the lumen or lumens around a pulley, the lumens can be folded, accordion-fashion at their proximal ends and a drive employed to move the lumens along the needle (e.g., the stylet). The drive can be a pair of opposing rotating drive wheels that press against the proximal portion of the lumen (or a member attached to the lumen) and frictionally engage a portion of the lumen or a structure attached to it to drive the lumen along the stylet. Alternatively a capstan drive could be used with the lumens winding partially around it.

While in most of the embodiments described, a pair of lumens are described, one for vacuum and one for fluid, a single lumen providing vacuum at one time and fluid at another time could be employed. A switching mechanism provided at the proximal end could allow this alternative. In this case, the drive mechanism for the bulkheads would function as described with a single lumen running along the stylet rather than two.

Although in most of the disclosed embodiments, fluid is provided to the distal end of the needle and permitted to flow proximally as the tissue sample is transported proximally, the fluid itself need not, and in embodiments, preferably is not, sufficient in quantity or velocity to move the tissue sample. That is, preferably, the fluid rate does not produce enough drag on the sample, given the seal between the sample and the stylet, the fluid flow rate, and the hydrodynamic properties of the sample, to transport the sample along the stylet. The fluid is preferably provided to flood the sample chamber and lubricate the passageway for transport. In addition the fluid may be only sufficient to fill in the space behind the bulkhead or bulkheads so that they, and the tissue, move more freely without creating any vacuum, even momentarily, in their wake. Preferably, the bulkheads described in the disclosed embodiments to not form a seal with the stylet or cannula. In this way fluid can flow around them easily. In fact, the fluid used to lubricate movement of the bulkhead(s) and sample may be provided at the middle of the sample chamber or proximal of the sample chamber and allowed to flow around the bulkheads to aid in transporting and preventing a vacuum.

In addition to the transport function, the fluid also provides a cleaning function; clearing bits of tissue sample or aspirated material from the host from the stylet. In an embodiment that is a self-contained handheld, as is the preferred embodiment, the quantity of fluid should be minimal, but in other embodiments where large amounts of fluid can be provided, the fluid flush can be substantial and continue for a long interval after the sample is received at the recovery location.

Although in most of the disclosed embodiments, the transport mechanism relies on the lumen or lumens themselves to transport the bulkheads, the fluid carrying and bulkhead-transporting functions can be performed by separate elements.

BRIEF DESCRIPTION OF THE DRAWINGS

The accompanying drawings, which are incorporated herein and constitute part of this specification, illustrate presently preferred exemplary embodiments of the invention, and, together with the general description given above and the detailed description given below, serve to explain features of the invention.

FIG. 1B1 illustrates the distal end of the biopsy device embodiment of FIG. 1 with the cutting cannula retracted.

FIG. 1C1 illustrates a cut-away view of FIG. 1A with the cutting cannula and stylet removed for clarity.

FIGS. 1D and 1E are a close-up view of a distal end of the transport mechanism of FIG. 1A and other embodiments.

FIG. 1C1 illustrates the mechanism of FIG. 1B with the cutting cannula or cutter fully advanced.

FIGS. 1B2, 1C2, 1F2, 1F1, 1G, and 1H illustrate a sequence operations of a biopsy tissue extraction device.

FIG. 2A illustrates another preferred embodiment of a biopsy needle and transport elements.

FIG. 2B illustrates a cut-away view of the device of FIG. 2A with the cutting cannula or cutter retracted.

FIG. 2C is a view of the device of FIG. 2B showing cutting cannula.

FIGS. 2D-2H illustrate a sequence of biopsy tissue extraction operations using the device of FIG. 2A.

FIGS. 2I-2N illustrate saline pumping and recovery plumbing components which may be used for tissue transport and other operations such as vacuum suction.

FIGS. 3A-3C and 3E-3G illustrate an integrated biopsy marker system for each of the devices of FIGS. 1A and 2A.

FIG. 3D illustrates various markers usable with the system of FIG. 3A.

FIGS. 5A1, 5A2, 5A3, 5B, and 5C illustrate a further integrated biopsy marker system for each of the devices of FIGS. 1A and 2A.

FIGS. 6A and 6B illustrate yet another integrated biopsy marker system for each of the devices of FIGS. 1A and 2A.

FIGS. 7A, 7B, 8A, and 8B illustrate various components of an embodiment of a biopsy device with particular emphasis on the drive mechanism, the device having a disposable part and a durable part which mate to create an operable device.

FIG. 9 illustrates an alternative lumen and drive arrangement applicable to most of the embodiments.

FIG. 10 illustrates an alternative another lumen and drive arrangement applicable to most of the embodiments.

FIG. 11 illustrates a controller.

DETAILED DESCRIPTION OF THE PREFERRED EXEMPLARY EMBODIMENTS

Figures 1, 1A:
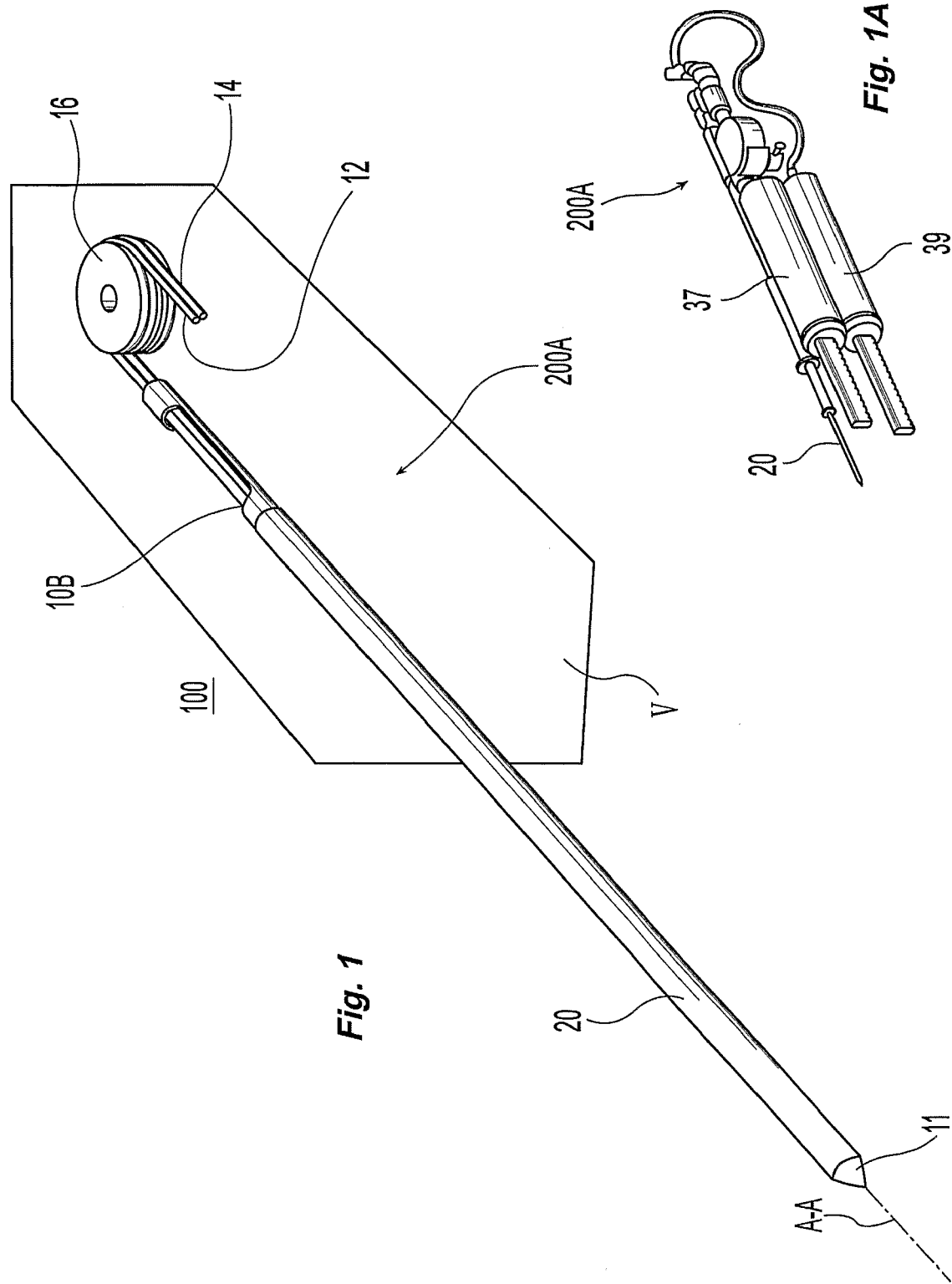
FIG. 1 illustrates a perspective view of a biopsy device and transport subassembly according to one exemplary embodiment of the present invention.
FIG. 1A illustrates an exemplary embodiment of ancillary components for the biopsy cutter and transport assembly of FIG. 1.

FIGS. 1-6 illustrate the preferred exemplary embodiments. In particular, FIG. 1 shows a perspective view of a stylet 10 coupled to the single-insertion, multiple samples biopsy device 100 provided with a transport subassembly 200A. The transport subassembly 200A includes the stylet, which has a tip 11 at the distal end and an outer cutting cannula 20 covering a substantial portion of the stylet 10 and a first port 10A. Extending through a hollow portion of the stylet 10 are two flexible lumens 12 and 14 coupled to a common pulley 16 proximate a second port 10B. The transport subassembly 200A can be coupled to ancillary components of the device 100 such as respective saline 37 reservoir and pump and vacuum and air pressure pump 39, a motor drive 200A, and switches and sensors as shown in FIG. 1A.

Referring to FIG. 1D, the flexible lumens 12 and 14 are coupled to a first bulkhead 18. A second bulkhead 22 is coupled to the first bulkhead via a rigid lumen 24. One of the flexible lumens 12 and 14 can be in fluid communication with a pressurized or negative pressure (i.e., vacuum) source. The other of the flexible lumens 12 and 14 can be in fluid communication with a bio-compatible fluid such as, for example, saline. In the illustrated embodiment, preferably lumen 14, which is fluidly continuous with lumen 24, carries liquid, such as saline and the lumen 12, which opens on the distal side of the first bulkhead 18, carries air under either positive pressure or vacuum.

The first bulkhead 18 can be configured to be disposed in the hollow stylet 10 in the manner of a piston loosely reciprocating in a cylinder arrangement. To avoid a pressure being generated, the first bulkhead and the stylet 10 can be configured such that they do not form a seal between them, for example, by sizing the first bulkhead 18 accordingly or by providing ports through it. To allow fluid flow between the second bulkhead 22 a bulkhead, similar in structure to the first bulkhead 18 is used, except that grooves 22B are provided (for example by machining or molding) on the outside surface of the bulkhead 22. These grooves 22B allow fluid to pass in a proximal direction into the first port 10A from the distal side of the second bulkhead 22 after being conveyed there through lumen 24. Alternatively, a through-opening 22C can be provided for the second bulkhead 22 instead of, or in addition to, the grooves 22B to provide a similar effect. Preferably, the lumens 12 and 14 are sufficiently flexible to allow them partly wound about a pulley 16 (See, for example, FIG. 1G) and that the rigid lumen may be, and preferably is, rigid.

Referring to FIGS. 1B1 and 1B2, the outer cutting cannula 20 is shown in a retracted position. This is preferably done after inserting the tip portion TP in a host where a tissue sample BSM is be excised and recovered. The retracted cannula 20 exposes the first port 10A formed by the hollow portion of the stylet 10. A sample of the biological tissue can be captured by providing a vacuum via one of the flexible lumens 12, 14; preferably 12 as discussed above, so that biological tissues are drawn into the first port 10A by the suction. In addition, a user may apply external pressure to the host to assist in moving tissue into the first port 10A.

The first port 10A has an internal volume V defined by the two bulkheads 18 and 22 and the inside surface of the cutting cannula 20. For a 14 gauge stylet or needle, the internal volume is sufficient to capture a mass of at least 50 milligrams of biological tissues, e.g., test tissues such as turkey breast tissues. For a 10 gauge stylet 10, the internal volume is sufficient to capture a mass of at least 150 milligrams or more of biological tissues. The length of the stylet 10 can be of any suitable lengths, such as, for example, about 250 to about 300 millimeters. The volume V of the housing containing all of the components of the device 100 is preferably about 0.32 cubic centimeters with particularly preferable dimensions of about 40 millimeters by about 40 millimeters and about 200 millimeters.

As used herein, the term "about" or "approximately" for any numerical values indicates a suitable dimensional tolerance that allows the part or collection of components to function for its intended purpose as a biopsy cutter, biopsy system or the combination of both the system and cutter.

Details of the lumens 12, 14, and 24 are explained with reference to FIGS. 1D and 1E. In FIG. 1D, two flexible lumens 12 and 14 are coupled to a proximal or first bulkhead 18 with one of the flexible lumens 12 or 14 being coupled to a rigid lumen 24, which is coupled to a distal or second bulkhead 22. Both the proximal bulkhead 18 and the distal bulkhead 22 are configured to allow the flow of saline to be dispersed through between the two bulkheads 18 and 22.

Referring back to FIGS. 1B1 and 1C1 (also FIGS. 1B2 and 1C2), once the tissue sample BSM is suctioned into the tissue receiving trough or first port 10A via the flexible lumen 12, the cannula 20 is advanced to separate the biological tissue BSM from the larger main mass of biological tissue. The cutting action by the cannula 20 can be by translation, rotation, translation and rotation or a combination of these movements along with back and forth axial movements of the cannula 20 as part of the cutting strategy. The cutting cannula 20 can form somewhat of a seal with the stylet tip 11 at full extension of the cutting cannula 20 along the longitudinal axis A. At this point, the pulley 16 (FIG. 1G) can be used to retract both bulkheads 18 and 22 towards the pulley 16 (i.e., proximally). At the same time saline S is delivered through the saline lumen 24 to enter a gap formed between the distal bulkhead 22 and the stylet 10. The saline flows back out of the gap through the openings formed by the grooves 22A and/or the port 22C into the port 110A, while the bulkheads 18 and 22 are retracted using the pulley 16. The saline wash lubricates the acquired tissue sample BSM (and the moving bulkheads 18 and 22) as the sample is retracted through the hollow portion of the stylet 10, as shown in FIGS. 1F1 and 1F2.

Once the tissue sample BSM is transported to the second port 10B, the tissue sample can be expelled into a collection vial or receptacle (not shown) using a suitable ejection mechanism such as, for example, saline solution S, pressurized fluid P or air a combination of both, as shown in FIG. 1H. To accomplish this, fluid and/or air may be forced through one or both of lumens 12 and 14.

In the variation shown in FIGS. 2A-2H, an alternative transport subassembly 200B to transport the tissue sample BSM towards the second port 10B is provided. Specifically, the mechanism includes a stylet 10 surrounded for a portion with a cutting cannula 20 and a sleeve disposed between the stylet 10 and the cannula 20. The stylet 10 includes a tipped portion 11A and hollowed portion 11B, flexible saline tubing 34 28 coupled to an intermediate sleeve 26 via a manifold 32, which is coupled to a secondary transport pulley 30. The flexible vacuum lumen 12 is coupled to a proximal bulkhead 18 at one end and a tissue transport pulley 16 at an intermediate portion of the flexible lumen 12. Referring to FIG. 2B, the stylet tip 11 can be a substantially solid and generally symmetric cone tip coupled to a hollow elongated portion 11B bounded by the bulkhead 18, which is connected to the flexible vacuum lumen 12. With the stylet 10 inserted into a host, the cutting cannula 20 and intermediate sleeve 26 are retracted, as shown in FIG. 2C. In this position, the first port 10A is exposed to allow a tissue sample BSM to be drawn into a trough defined by the interior volume of the stylet 10 and the bulkhead 18. The tissue sample BSM that can be captured in the first port 10A can be substantially the same mass as that of the device of FIG. 1A. However, due to the elimination of the distal bulkhead and the rigid saline lumen, the mass of biological tissues that can be captured can occupy a greater fraction of a corresponding needle axial length in this embodiment.

The sequence of operations for tissue transport are illustrated in FIGS. 2C-2H. In FIG. 2C, the cutting cannula 20 and intermediate sleeve 26 are retracted proximally to expose the first port 10A while the cannula 20 is in the host. Vacuum is applied through the lumen 12, thereby creating a vacuum in the first port 10A. This draws the tissue sample BSM into the first port 10A. Then the cutting cannula 20 is extended distally, as shown in FIG. 2D, to sever the tissue sample BSM from the host. The tissue sample BSM is now contained and ready for transport to the second port 10B.

Referring to FIG. 2E, the intermediate sleeve 26 is extended distally to cover the first port 10A. Preferably, the first port 10A is only partly covered so that a gap is provided between the outer surface of the intermediate sleeve 26 and the inner surface of the cannula 20. This gap allows saline fluid to flow through the gap to fill the first port 10A after being pumped from the proximal end in the annular space between the outer cannula 20 and the intermediate sleeve 26. The intermediate sleeve 26 is connected at a proximal end to a manifold 32 located between first and second ports, shown here in FIG. 2F. The manifold 32 is coupled to the flexible saline tubing 34, which is coupled to the secondary transport pulley 30 (indicated by the reference numeral in FIG. 2A and visible in FIG. 2F as well). so that upon rotation of the secondary transport pulley 30, the manifold 32 is moved distally or proximally. As the manifold 32 is moved, an end cap 32A of the intermediate sleeve 26 is also movable (FIG. 2F) due to a connection between the end cap 32A and the manifold 32. The end cap 32A allows for saline to flow from the tubing 34 to the manifold 32 and through the gap between the cutting cannula 20 and the sleeve 26 towards the first port 10A (FIG. 2E) to provide lubrication for the moving lumen, provide a preservative, and provide a liquid flush for any loose remnants of tissue samples. The tissue BSM can be ejected into the collection chamber 36 by at least the saline S flowing through the hollow stylet. Alternatively, pressurized fluid or liquid can be provided via the lumen 12 to eject the tissue sample, alone or in combination with the saline S. The rate of saline flowing can be, and preferably is, increased for ejection purposes over the rate used to transport the tissue sample BSM.

Although only one tissue collection chamber 36 is shown, the chamber 36 can be a plurality of chambers disposed about the stylet 10 in a radial pattern so that the chambers can be rotated to accept tissue samples each time the transport 200A or 200B is activated to transport a sample to the second port 10B. The vacuum source can be used to remove excess fluid from the stylet 10/sheath 26 assembly after the sample BSM is ejected. The vacuum may also help to aspirate fluid from the host that was drawn into the stylet 10/sheath 26 assembly.

In an alternative embodiment, the intermediate sleeve 26 can be omitted and fluid may be pumped between the outer cannula 20 and the stylet 10. In this embodiment, the stylet 10 fits into the outer cannula 20 with a close spacing, preferably with a spacing (difference between stylet outer diameter and outer cannula inner diameter) between 1 and 6 thousandths of an inch and more preferably with a spacing between 1 and 3 thousandths of an inch. In this case, fluid may not be conveyed to the distal end of the sample recess 10A, but will still be effective, particular in small gage needles, for example 14 gage needles, to adequately facilitate transport of the sample.

Figure 2M:
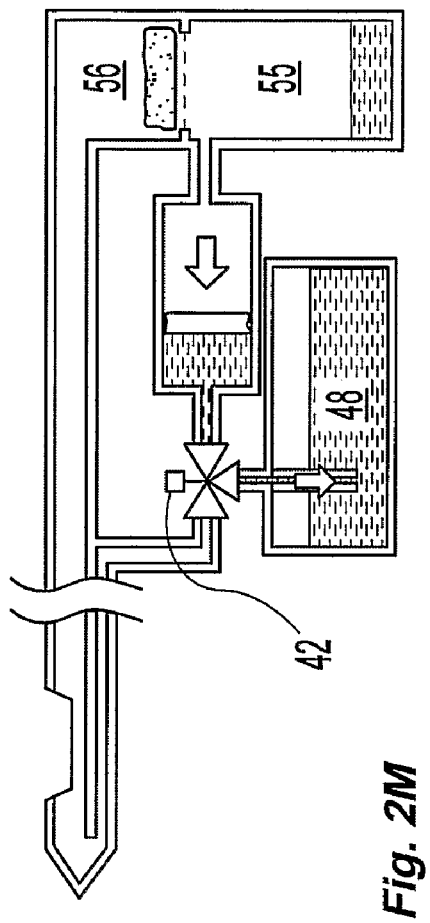

FIGS. 2I-2N describe a saline pumping mechanism that may be used with the above and other embodiments. In FIG. 2I, a dual-action pump 40 (e.g., a syringe actuatable by a drive motor) can be used to generate negative pressure by forcing a piston 46 to expand the volume of a chamber 40A, which is in communication with the main passage 10F of the stylet 10. A four-way valve 44, with a vent 42 at one branch, is configured to empty the chamber 45 to the ambient through the four-way valve and out the air vent 42 as air is sucked into the chamber 40A. Note that the vent 42 may be fitted with a filter to prevent contamination leaking into the biopsy device.

The vacuuming action draws in a tissue sample 53. To trigger the cutting of the sample, sensors (not shown) may be used to detect the movement of the tissue sample 53 into the lumen 10G, or the passage of an elapsed time interval or user action may be used to determine that a sample 53 has been drawn into the passage 10G. The outer cannula 20 can be used to sever the tissue sample from the host. Alternatively, a cannula disposed internally of the stylet 10 can also be used.

At this point, shown here in FIG. 2J, the four-way valve 44, with a vent 42 at one branch, is configured to allow the dual-action pump 40 to draw saline into port 40B. With the outer cannula 20 covering the port 10A (not shown for clarity), the dual-action pump 40, via the four-way valve 44, forces saline to flow through passage 10B, causing the tissue sample to be transported proximally towards through-port 10B (e.g., FIGS. 1, 2A). As the sample encounters the mesh material 39B in a collection vial or cartridge, it remains in place while residual saline falls into the sump 55. Any remaining saline in the lumens can be drawn back into the reservoir 48 by first drawing from the lumens into the chamber 45 (FIG. 2L) and then pumping into the reservoir 48 (FIG. 2M) for subsequent use by the dual-action pump 40.

Figure 2N:
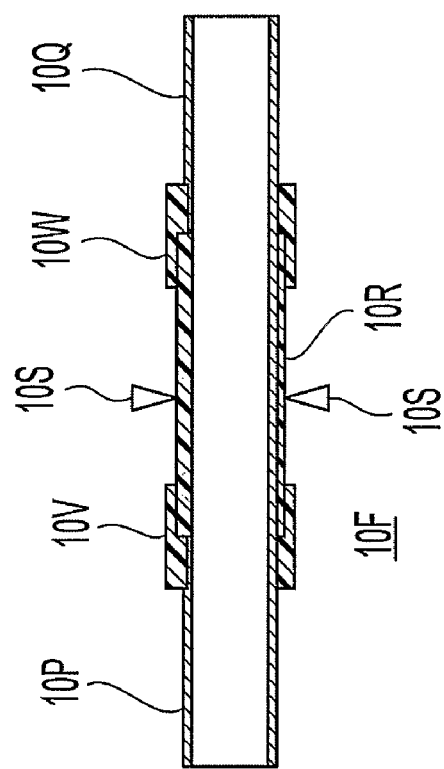

Referring to FIG. 2N, in an alternative embodiment, the passage 10F is provided with a flexible tube segment 10R that can be pinch-clamped by means of a valve actuator 10S. In this configuration, a pair of inline connectors 10V and 10W provides a smooth transition from a lead in part 10P to a lead out part 10Q to allow fluid and samples to pass through as in the earlier embodiment of passage 10F. The reason for adding this capability to close the valve is to allow a stronger vacuum to be developed in the sample area 10A by improving the volumetric efficiency of the dual action pump 40. To apply a vacuum to sample port 10A, the piston valve is configured to draw from the lumen 10B. The clamp 10S is closed. The piston 46 is moved to the right to generate the vacuum by expanding the volume of chamber 45. Because the passage 10P is closed, the total volume evacuated, relative to the chamber volume 45, is markedly decreased. This configuration of passage 10P also has the advantage of avoiding the need for vacuum-competent sealing of the collection chamber 56 and sump 55.

The examples shown in the illustrations and described in detail above can be integrated with one or more of four exemplary marking systems. In particular, each of four marking systems can be integrated with each of the two examples described to provide for eight different integrated biopsy cutter and marker systems. For clarity, only the four marking systems will be described and shown below. However, those skilled in the art can combine each marker system with each of the biopsy cutter systems as appropriate to arrive at a suitable permutation of biopsy sampling device and integrated marker.

Referring to FIGS. 3A-3G, a marker system utilizing a hook type marker 41 (i.e., a "harpoon") to prevent migration of the marker 41 once it has been deployed, is shown. The hook type marker 41 can be deployed in sequence or simultaneously with the sampling of biopsy tissues with the various technologies described in relation to FIGS. 1 and 2 above. As shown in FIGS. 3A and 3E, a rod (e.g., an internal D-Rod 20A or the cutting cannula 20) can be used to eject a marker 41 stored in the stylet tip 11. In the exemplary embodiment of FIGS. 3A-3G, a rod 20A is provided with a cut-out portion 20B having a ramp 20C formed on a distal end of the rod 20A. The ramp 20C can be used (depending on whether the cannula 20 or rod 20A is axially translated only, rotated only or a combination of axial translation and rotation) to ensure that the marker 41 is deposited sufficiently near the tissue sampling site. Various marker configurations can be utilized. For example, marker with wire like hooks 41A, square sectioned hook 41B, or marker with serrated edges 41C can be used in this system. Alternatively, the first and second bulkheads 18 and 22 (FIG. 1B2) can be provided with a recess for storage of a marker 41 so that upon actuation of the inner cannula 20A, a first marker can be released from the first bulkhead 18, a second marker from second bulkhead 22, and a third marker 41 can be released from the tip 11 upon actuation of an internal cannula 20A (FIG. 3A) to close port 10A.

Figure 4B:
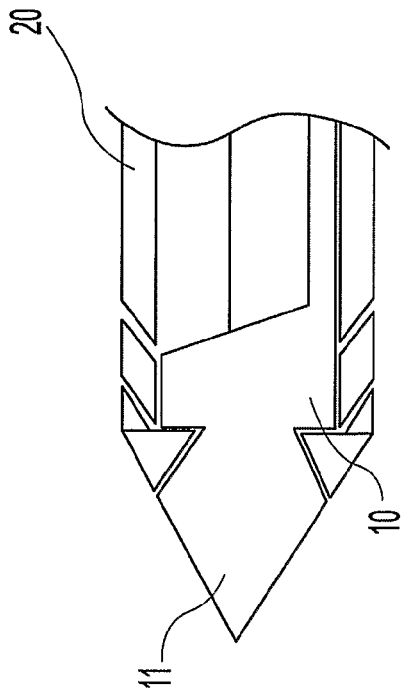
FIGS. 4A-4D illustrate another integrated biopsy marker system for each of the devices of FIGS. 1A and 2A.
Figure 4D:
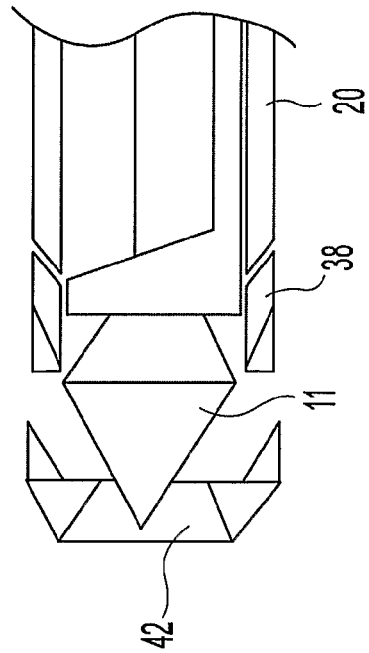
Figure 4A:
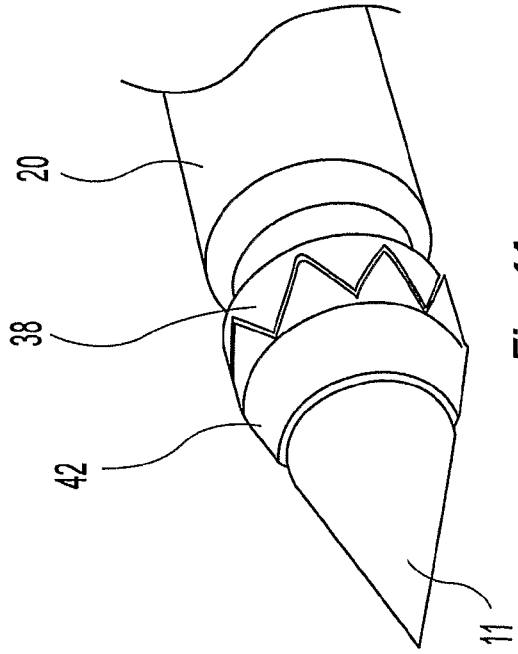
Figure 4C:
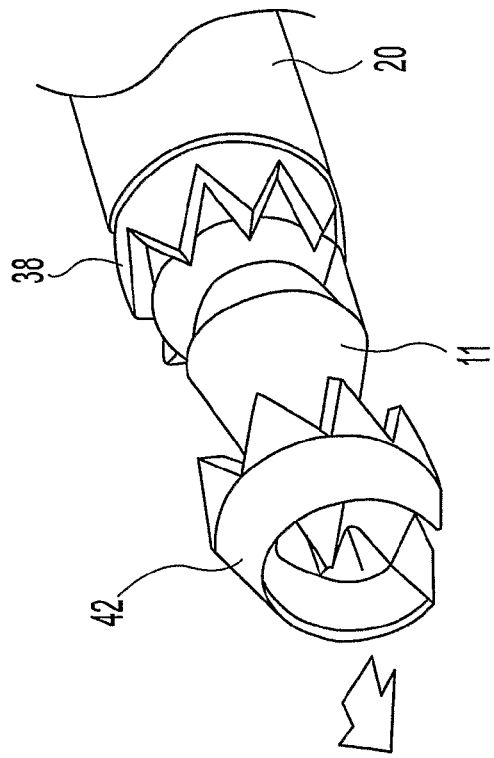

Referring FIGS. 4A-4D, a marker system utilizing a split ring marker 42 can be utilized with various biopsy techniques described above in relation to FIGS. 1 and 2. In FIG. 4A, the split-ring marker 42 can be mounted to the stylet 10 via a suitable technique such as, for example, crimping, swaging or semi-permanent bonding. Optionally, an intermediate member 38 that forms a seal with the cannula or cutter 20 can be provided to maintain a generally constant outer diameter of the cannula 20 without an abrupt transition to the tip 11. The split-ring marker 42 can be deployed by itself, simultaneously with the sampling of the tissue, prior to sampling or subsequent to the sampling. As shown in FIG. 4B, the stylet tip 11 can be actuated proximally towards the user to force the split-ring marker 42 to detach from the tip 11. Alternatively, the cutting cannula 20 can be actuated distally away from the user to force the split-ring marker 42 to separate from the stylet tip 11.

Referring to FIGS. 5A1, 5A2, 5A3, 5B and 5C, a marker system using a blossom-type marker 44 can be utilized with various biopsy techniques described above in relation to FIGS. 1 and 2. As shown in FIG. 5A, the blossom marker 44 is mounted on a specially configured stylet tip 110 (FIG. 5C), which has grooves 112 and ramps 114 disposed about a longitudinal axis of the tip 110. The blossom marker 44 can be mounted by a suitable technique, such as, for example, crimping, swaging, or casting onto the specially configured stylet tip 110. As shown in FIG. 5B, the cutting cannula 20 can be moved distally away from the user to force the blossom marker to be separated from the stylet tip 11. As the marker 44 is separated from the tip 110, the ramps 114 on the tip 110 force the sectioned tips 44A to blossom, thereby forming hooks 44A. Alternatively, the stylet tip 11 can be actuated proximally towards the user so that the marker is deployed via contact against the cutting cannula 20.

Referring to FIGS. 6A and 6B, another marker system is shown which uses a spiral-type marker 46 in conjunction with various biopsy systems described above in relation to FIGS. 1 and 2. As shown in FIG. 6A, a coiled marker wire 46 can be disposed in a hollow proximal section 111 of the stylet tip 11. A suitable deployment mechanism can be used to eject the coiled marker wire out of its storage space in the stylet tip 11. The deployment mechanism can be a suitable mechanism, such as, for example, a linear-to-rotary motion converter that converts a linear motion into a rotary motion to rotatably expel the marker.

The materials suitable for use as part of each marker can be, for example, stainless steel, gold, titanium, platinum, tantalum, barium sulfate, biodegradable iron or shape memory polymer or metal alloy such as Nitinol. It is noted that Nitinol is radio-opaque, ultrasonically opaque and MRI compatible and therefore would be preferred by itself or in combination with other materials described herein and as known to those skilled in the art. Further, the markers can be of any suitable size so that it can be fitted onto a 7, 8, 9, 10, 11, 12, 14, or 16 gauge needle.

Although the markers have been shown as a single deployment marker, some of the embodiments disclosed herein can be utilized in a multiple deployment aspect. For example, the tip 11 can be configured to store a plurality of harpoon markers 41; the stylet 10 can be mounted with a longitudinal series of split-ring markers 42; the tip 11 can be configured with a cutter so that multiple helical markers can be deployed.

Referring to FIGS. 7A, 7B, 8A and 8B, a disposable component 251 mates with a durable component 250 to form a biopsy device 201. The disposable component carries an cutting cannula 220, which functions as the cutting cannula 20, described above, for example with reference to FIGS. 1B1 to 1H. The cutting cannula 220 is moved along its axis in distal and proximal directions by a worm gear 266 that threads with a nut 274 mounted in a disposable chassis 268. When the disposable chassis 268 is mounted in the durable component 250, a gear 256 meshes with a pinion 270 of a cutter drive 290 housed in the durable component 250. The worm gear 266, which is connected to the gear 256 is thus rotated by the cutter drive 290 advancing and retracting the cutting cannula 220.

The disposable chassis 268 may be connected to further elements (not shown) to support a pulley 216, a motor 288 that drives the pulley 216, and an encoder 280 that is used to control the position of the pulley 216. The additional elements carried with the disposable chassis 268 may include fluid and vacuum circuit 260. The durable component 250 may carry various motor drives including the drive 290, a pulley drive 292 and a peristaltic pump 284.

In the present embodiment, the pulley 216 is a component of the pulley drive 290. Its functions are essentially the same as for the pulley 16 described above, for example with reference to FIG. 1. In the present embodiment, bulkheads 218 and 222, rigid lumen 224, flexible lumens 212 and 214, a sampling port 210A, a recovery port 210B, and a stylet 210 with a tip 211 all function as the bulkheads 18 and 22, rigid lumen 24, flexible lumens 12 and 14, sampling port 10A, recovery port 10B, and the stylet 10 with tip 11 described above. A sample chamber 258 may be provided at the recovery port 210B to capture and protect the sample once ejected from the recovery port 210B.

A slack extension 276 of flexible lumens 212 and 214 is stored in an enclosure 252 which allows the slack extension 276 to unroll and wind up as the flexible lumens 212 and 214 are extended and withdrawn by the pulley 216. The slack extension 276 is shown as it would appear when the slack is used up by extending the lumens as well as as it would appear when the slack is stored by retracting the lumens. So though two loops are shown at 276, it is only actually one loop shown in both the extended and retracted positions. An encoder 280 is used to control the position of the bulkheads 218 and 222 within the cutting cannula 220. The pulley 216 may be driven by a motor 288 affixed to the durable component 250.

A guide tube 278 holds the flexible lumens 212 and 214 as they are moved along the axis of the cutting cannula 220. The flexible lumens 212 and 214 may be relatively stiff along lengths that do not need to be greatly strained during the movement of the bulkheads 218 and 222. For example the portions of the flexible lumens 212 and 214 that run through guide tubes 278 and cutting cannula 220 may be relatively stiff compared to the portions that wrap around the pulley 216. Preferably the flexible tubes 212 and 214 are inelastic in tensile and compression modes. Also, preferably, the stiffness and inelasticity are such that the tissue shuttle can be moved through the biopsy needle in a predictable and repeatable way by pulling and pushing the lumens 212, 214.

Within the guide tube 278 and cutting cannula 220, there may be one or more bulkheads 242 to help maintain a straight trajectory of the flexible lumens 212 and 214. The spacing may be determined according to the flexibility of the flexible lumens 212 and 214 to ensure that the movement of the bulkheads 212 and 214 is predictable and consistent, thereby enabling control of the latter by means of the encoder 280 located on the pulley 216. A gap between the end of the cutting cannula 220 and the guide tube 278 gives the cutting cannula 220 room to move over its axial range.

A controller (not shown) may be configured to control the drives 288 and 290 such that the following operation sequence can be realized to obtain a sample and deliver the sample to the port 210B. The procedure may be as follows.

1. Upon insertion of the disposable component 251, assert a home position in which the cutting cannula 220 and the flexible tubes 212 and 214, along with the connected bulkheads 222 and 218, are fully extended toward the distal end. This may be done by running drives 288 and 290 to registration positions, where respective (limit) switches triggered, and counting the pulses of respective encoders. The indication of insertion may be by means of switch (not shown) on the durable component 250 triggered by a boss (not shown) on the disposable chassis 268. The registration may be followed by the retraction of the chassis 268 in preparation for a thrusting operation as is known for biopsy needles.
2. Upon receipt of a command (e.g., a control panel switch) to obtain a sample, a vacuum pump (not shown, but preferably a component such as a syringe is provided in the disposable component 251 and a mating drive is provided in the durable component 250) is operated to obtain an initial vacuum.
3. As soon an initial vacuum is generated, the cutting cannula 220 is retracted by running the drive 288 while counting pulses of the encoder 280 to a proximal stop point. Alternatively control signaling can be provided by a limit switch.
4. After a programmed interval, following the retraction of the cutting cannula 220, the cutting cannula 220 is driven distally by operating the motor/transmission drive 290 while counting pulses of an encoder to a distal stop point. Alternatively control signaling can be provided by a limit switch.
5. The flexible tubes 212 and 214 are retracted by running the drive 288 to bring the gap between the bulkheads 222 and 218 to the port 210B while flushing saline in a proximal direction. This may be done by running the peristaltic pump 284 and counting pulses of the encoder 280 to a proximal stop point or according to signals of a limit switch.

6. After the sample reaches the port 210B, the sample may be ejected as described above, for example using a puff of air or saline or both. The sample may then be housed in the sample chamber 258 or any of the cartridge embodiments described above.

In the above-described embodiments, the one or more lumens extending through the needle (e.g., the stylet) can be, and preferably are, rigid along their length within the needle and flexible only along portions that are required to bend. This ensures that the lumens can be used to push the corresponding transport members (e.g., bulkhead(s)) for multiple sampling. In this case, "flexible" is intended to encompass piece-wise flexible such as fluid conveyances that are made up with multiple hinged elements as links in a chain. There are known and commercially available devices that flex but provide fluid-tight flow channels.

In addition, the rigidity of the lumens can be derived from a secondary element that houses the lumen to give it rigidity, meaning a rigid portion of a lumen does not need to be a monolithic structure and the uses of terms such as "rigid lumen" or "rigid portion of a lumen" are not intended to limit the identified lumen structures to single-element structures. For example, a flexible lumen can be guided by a rigid member (for example it can slide within a tube) giving it all the effective rigidity needed to enable the lumen to move a transport member distally within a needle. Or a flexible tube can have a moving rigid guide (tube or other structure) to which it is fixedly attached, to give it all the effective rigidity needed to enable the lumen to move a transport member distally within a needle.

Referring to FIG. 9, an alternative drive to the above-described embodiments employs a folding, rather than winding lumen take-up mechanism. Instead of winding the proximal end or ends of the lumen or lumens around a pulley, the lumens 302 can be folded, accordion-fashion 306 at their proximal ends and a drive 300 employed to move the lumens along the needle 310 (e.g., the stylet). The lumen or lumens may be provided with natural kinks 305 between rigid portions 307 so that it folds naturally when driven proximally. Only a portion of the lumens 302 would need to have the kinks 305. As an example, the drive 300 can be a pair of opposing rotating drive wheels 312 that press against the proximal portion of the lumen 302 (or a member attached to the lumen) and frictionally engage a portion of the lumen or a structure attached to it to drive the lumen 302 along the stylet 310. Alternatively a capstan drive (not shown) could be used with the lumens winding partially around it. The bulkheads 304 and 305 are thereby moved as described in the other embodiments and in other respects this embodiment conforms to their alternative descriptions.

While in most of the embodiments described, a pair of lumens are described, one for vacuum and one for fluid, a single lumen providing vacuum at one time and fluid at another time could be employed. A switching mechanism provided at the proximal end could allow this alternative. In this case, the drive mechanism for the bulkheads would function as described with a single lumen running along the stylet rather than two.

Although in most of the disclosed embodiments, fluid is provided to the distal end of the needle and permitted to flow proximally as the tissue sample is transported proximally, the fluid itself need not, and in embodiments, preferably is not, sufficient in quantity or velocity to move the tissue sample. That is, preferably, the fluid rate does not produce enough drag on the sample, given the seal between the sample and the stylet, the fluid flow rate, and the hydrodynamic properties of the sample, to transport the sample along the stylet. The fluid flow rate, in a preferred embodiment where fluid economy is paramount, such as a self-contained handheld device, may preferably provide enough fluid to flood the sample chamber and lubricate the passageway for transport. Further, in addition, the fluid may be only sufficient to fill in the space behind the bulkhead or bulkheads so that they, and the tissue, move more freely without creating any vacuum, even momentarily, in their wake. That is, the fluid conveyance would convey fluid into the stylet as the sample is moved to fill an expanding space remaining distal of the sample and bulkhead as the bulkhead moves proximally.

Preferably, the bulkheads described in the disclosed embodiments to not form a seal with the stylet or cannula. In this way fluid can flow around them easily. In fact, the fluid used to lubricate movement of the bulkhead(s) and sample may be provided at the middle of the sample chamber or proximal of the sample chamber and allowed to flow around the bulkheads to aid in transporting and preventing a vacuum.

In addition to the transport function, the fluid also provides a cleaning function; clearing bits of tissue sample or aspirated material from the host from the stylet. In an embodiment that is a self-contained handheld, as is the preferred embodiment, the quantity of fluid should be minimal, but in other embodiments where large amounts of fluid can be provided, the fluid flush can be substantial and continue for a long interval after the sample is received at the recovery location.

Although in most of the disclosed embodiments, the transport mechanism relies on the lumen or lumens themselves to transport the bulkheads, the fluid carrying and bulkhead-transporting functions can be performed by separate elements. For example, as illustrated in FIG. 10, a stuff but flexible member 334, such as a spring steel band or wire, wraps around a take-up drum 328 which is rotated by a motor (not shown). The lumens 332 are flexible and passively move with the bulkhead 304. The flexible tubing fold 335 or even simply coil since it can be highly flexible in this embodiment.

Referring to FIG. 11, in all of the above embodiments, various motors, drives, valves, and other actuators are variously described along with their respective operations and operational sequences. It is clear from the particulars of each embodiment that a device may employ a controller 350 such as a programmable microprocessor controller, to provide the described functionality.

While the present invention has been disclosed with reference to certain preferred exemplary embodiments, numerous modifications, alterations, and changes to the described exemplary embodiments are possible without departing from the sphere and scope of the present invention. Accordingly, it is intended that the present invention not be limited to the described exemplary embodiments, but that it have the full scope.

The invention claimed is:

1. A single-insertion, multiple sample biopsy device, comprising:
    a stylet extending along a longitudinal axis between a distal end and a proximal end, the stylet having a tip at the distal end and a hollow interior volume extending from a biopsy port proximate the distal end to the proximal end;
    a cannula that surrounds a portion of the stylet and movable along the longitudinal axis;
    a plurality of non-coaxial lumens disposed in the hollow interior volume, the plurality of non-coaxial lumens including a first lumen and a second lumen;

a first bulkhead movably disposed in the hollow interior volume of the stylet, the first bulkhead being drivably coupled to the plurality of non-coaxial lumens and coupled in fluid communication with the first lumen;

a second bulkhead movably disposed in the hollow interior volume of the stylet, the second bulkhead being spaced distally from the first bulkhead to define a biopsy sample volume therebetween;

a third lumen drivably coupled to the second bulkhead and extending between the first bulkhead and the second bulkhead, the third lumen being configured to provide a continuous extension of the second lumen through the biopsy sample volume to a location distal the second bulkhead, and wherein the first lumen, the second lumen, the third lumen, the first bulkhead and the second bulkhead are configured as a single drivable unit; and a transport subassembly configured to drivably move the first lumen, the second lumen, the third lumen, the first bulkhead and the second bulkhead as a single unit in the hollow interior volume of the stylet.

2. The device of claim 1, where the transport subassembly includes one or both of vacuum and pressurized fluid supply in fluid communication with one of the plurality of non-coaxial lumens and a pulley that engages at least one of the plurality of non-coaxial lumens to move the plurality of non-coaxial lumens, the third lumen, the first bulkhead, and the second bulkhead concurrently along the longitudinal axis.

3. The device of claim 1, wherein each of the first lumen and the second lumen include a rigid portion and a flexible portion.

4. The device of claim 3, wherein the rigid portion lies along a length within the stylet.

5. The device of claim 3, wherein the flexible portion lies at least partly outside of the stylet.

6. The device of claim 2, where the first bulkhead is configured to confront an interior surface of the stylet and the second bulkhead is configured to permit fluid flow between an outer perimeter of the second bulkhead and the interior surface of the stylet.

7. The device of claim 1, further comprising a releasable marker coupled to the tip of the stylet, where the releasable marker is one of an annular marker or a split-ring marker.

* * * * *